United States Patent
Herrmann et al.

(10) Patent No.: US 9,315,763 B2
(45) Date of Patent: Apr. 19, 2016

(54) PHOTOLABILE LATEX FOR THE RELEASE OF PERFUMES

(71) Applicant: FIRMENICH SA, Geneva (CH)

(72) Inventors: Andreas Herrmann, Geneva (CH); Damien Berthier, Geneva (CH); Nicolas Paret, Geneva (CH); Myléne Therrien, Geneva (CH)

(73) Assignee: Firmenich SA, Geneva (CH)

( * ) Notice: Subject to any disclaimer, the term of this patent is extended or adjusted under 35 U.S.C. 154(b) by 74 days.

(21) Appl. No.: 14/349,857

(22) PCT Filed: Sep. 28, 2012

(86) PCT No.: PCT/EP2012/069208
§ 371 (c)(1),
(2) Date: Apr. 4, 2014

(87) PCT Pub. No.: WO2013/050303
PCT Pub. Date: Apr. 11, 2013

(65) Prior Publication Data
US 2014/0275288 A1    Sep. 18, 2014

(30) Foreign Application Priority Data

Oct. 6, 2011 (EP) .................................. 11184210

(51) Int. Cl.
| | |
|---|---|
| *A61K 8/81* | (2006.01) |
| *A61K 8/90* | (2006.01) |
| *C08L 31/02* | (2006.01) |
| *C11B 9/00* | (2006.01) |
| *C11D 3/50* | (2006.01) |
| *C08F 8/00* | (2006.01) |

(52) U.S. Cl.
CPC ............. *C11B 9/0015* (2013.01); *A61K 8/8152* (2013.01); *A61K 8/8158* (2013.01); *A61K 8/90* (2013.01); *C08F 8/00* (2013.01); *C08L 31/02* (2013.01); *C11D 3/505* (2013.01); *C08F 2800/10* (2013.01); *C08F 2810/20* (2013.01); *Y10T 428/2982* (2015.01)

(58) Field of Classification Search
CPC ............ C08F 8/00; C08F 8/02; C08F 220/14; C08F 220/18; A61K 8/8152
USPC .................. 424/489, 501; 512/4, 27; 524/505
See application file for complete search history.

(56) References Cited

U.S. PATENT DOCUMENTS 7,723,286 B2 *   5/2010  Fehr et al. ........................ 512/8

FOREIGN PATENT DOCUMENTS

| EP | 1 443 058 A1 | 8/2004 |
| WO | WO 99/60990 A2 | 12/1999 |

OTHER PUBLICATIONS

International Search Report and Written Opinion, application No. PCT/EP2012/069208, dated Dec. 21, 2012.
Marrero et al., "Group-contribution based estimation of pure component properties," Fluid Phase Equilibria, 183-184:183-208 (2001).

* cited by examiner

*Primary Examiner* — Alma Pipic
(74) *Attorney, Agent, or Firm* — Winston & Strawn LLP

(57) ABSTRACT

The present invention relates to the field of perfumery. More particularly, it concerns co-polymeric latex particles derived from 2-oxo-2-(3- or 4-vinylphenyl)acetates capable of liberating an active molecule such as, for example, an aldehyde or ketone upon exposure to light. The present invention concerns also the use of said latex in perfumery as well as the perfuming compositions or perfumed articles comprising the invention's latex.

20 Claims, 8 Drawing Sheets

Figure 1: Dynamic headspace analysis for the evaporation of pure 2-phenylacetaldehyde (---×---), or of 2-phenylacetaldehyde released from 2-phenylethyl 2-oxo-2-phenylacetate (...∆...) or from Latex 1a (—o—) in a fabric softener application
(a)
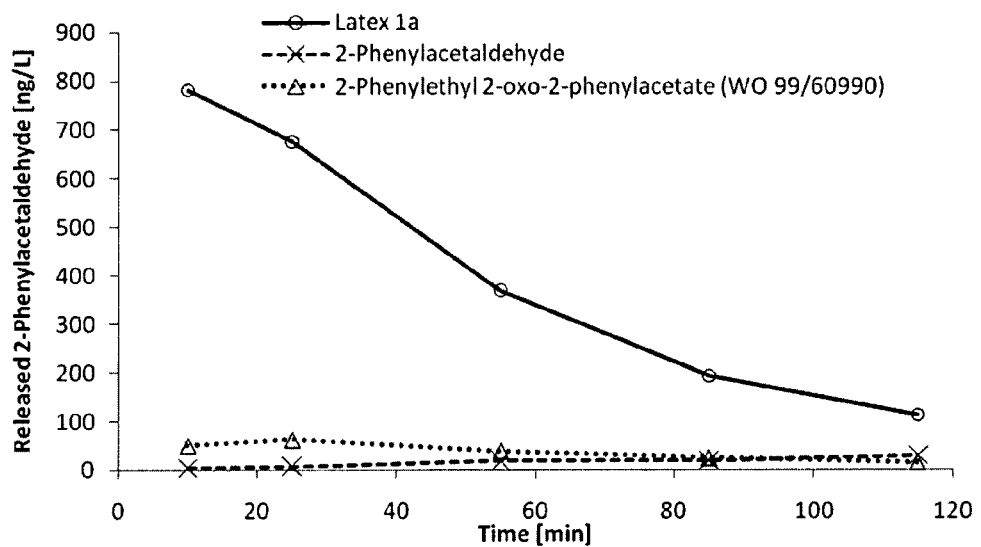
(b)
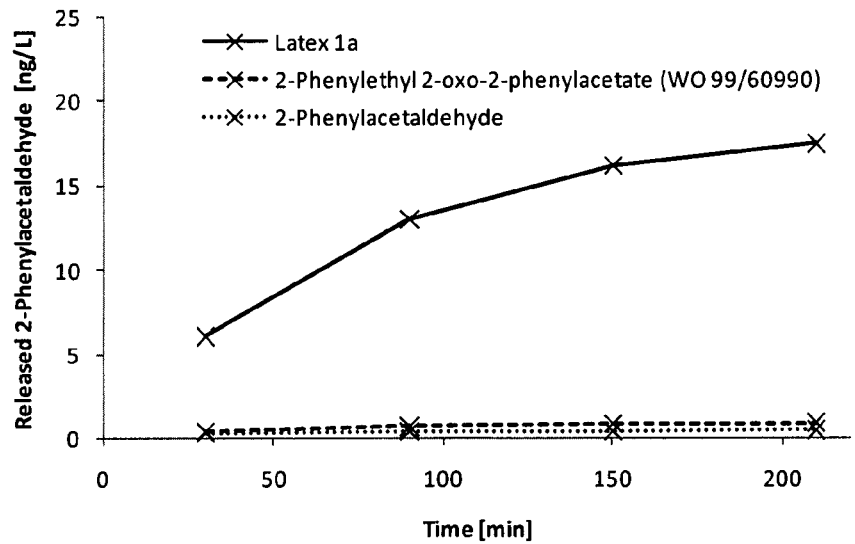

Figure 2: Dynamic headspace analysis for the evaporation of pure citral (---×---) or of citral released from Latex 2 (—◊—) in a fabric softener application
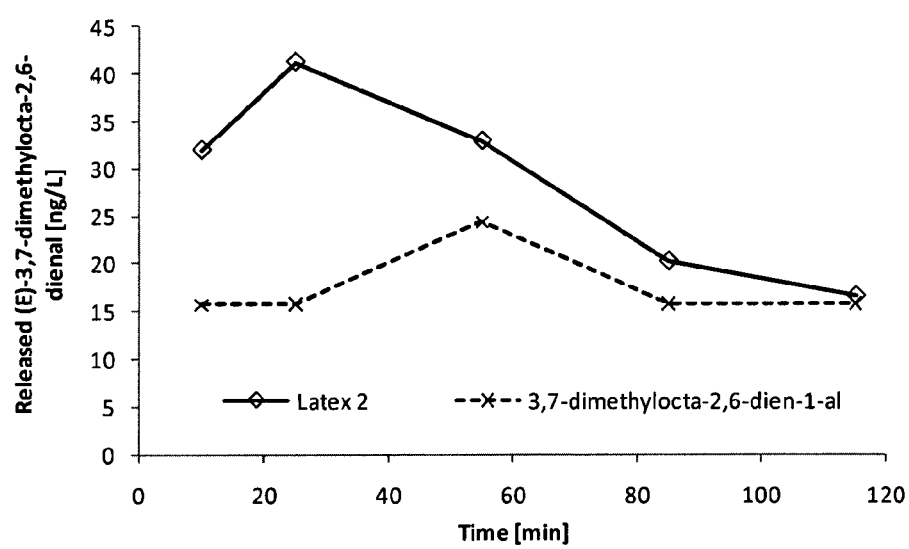

Figure 3: Dynamic headspace analysis for the evaporation of (Z)-3-hexenal (---×---) or of (Z)-3-hexenal from Latex 3 (—◊—) in a fabric softener application
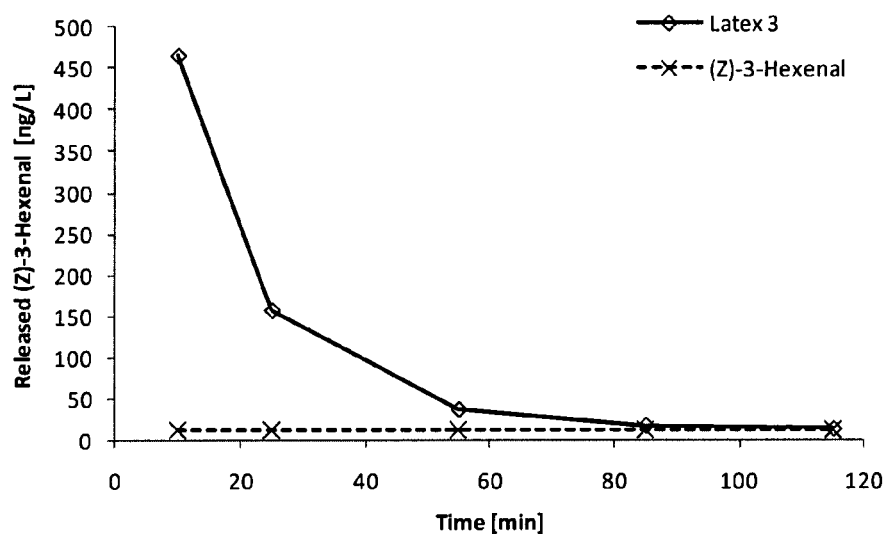

Figure 4: Olfactive panel evaluation of the intensity of the light-induced release of 2-phenylacetaldehyde from 2-phenylethyl 2-oxo-2-phenylacetate and from Latices 1a and 1b in a freshly prepared day cream
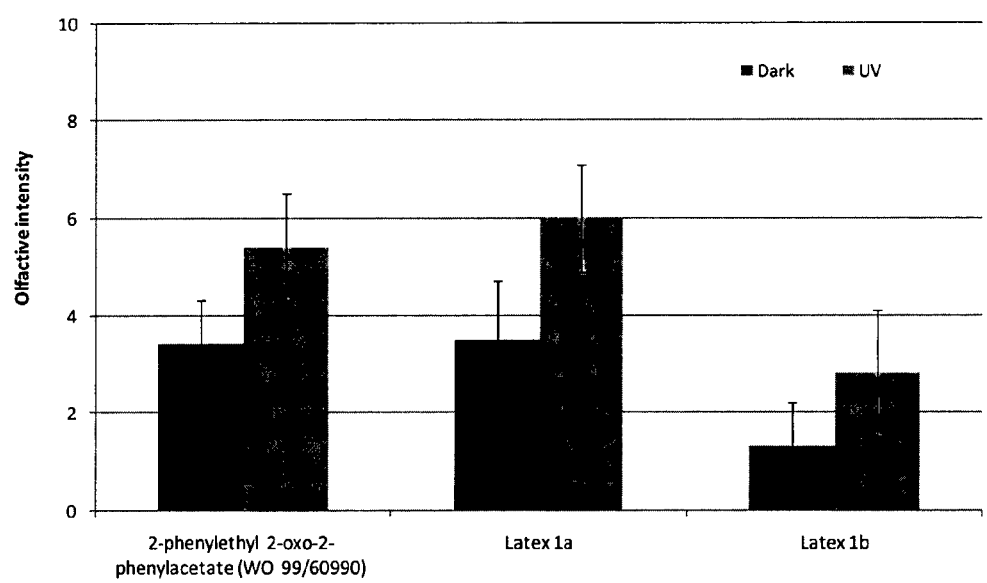

Figure 5: Olfactive panel evaluation of the intensity of the light-induced release of 1-decenal from Latex 5a in a freshly prepared day cream.
(a)
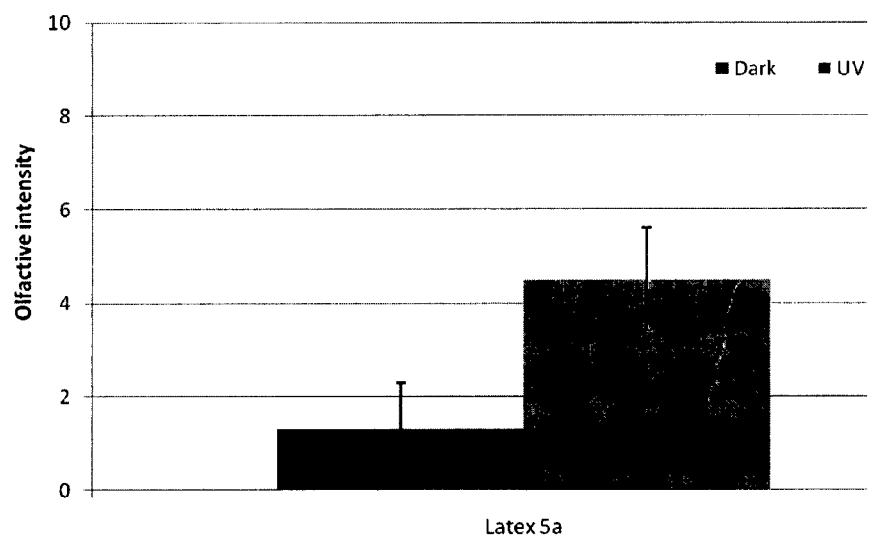
(b)
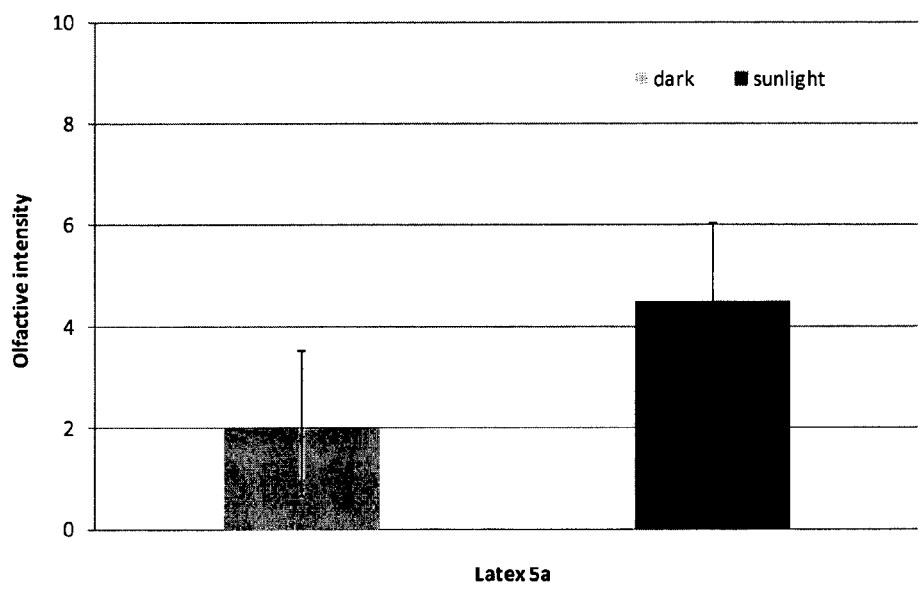

Figure 6: Olfactive panel evaluation of the intensity of the light-induced release of 2-phenylacetaldehyde from 2-phenylethyl 2-oxo-2-phenylacetate and from Latices 1a and 1c in a day cream after storage for 3 months at 45°C
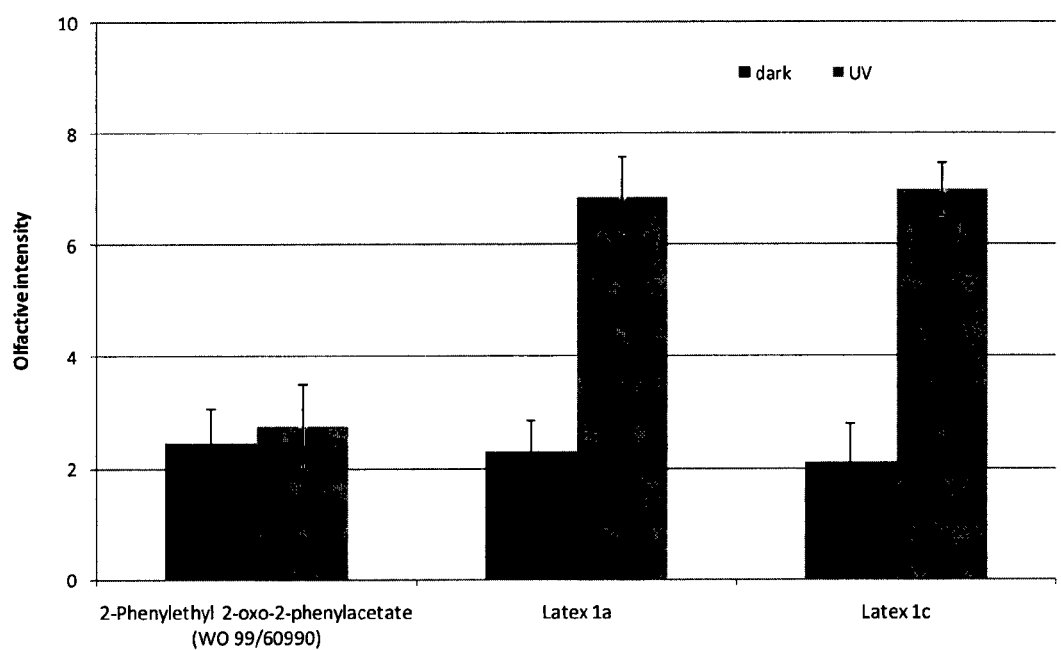

Figure 7: Dynamic headspace analysis for the evaporation of pure 2-phenylacetaldehyde (---×---), or of 2-phenylacetaldehyde released from Latex 1a (—o—) and for the evaporation of pure decanal (---×---), or of decanal released from Latex 5b (—o—) in an all purpose surface cleaner application
(a)
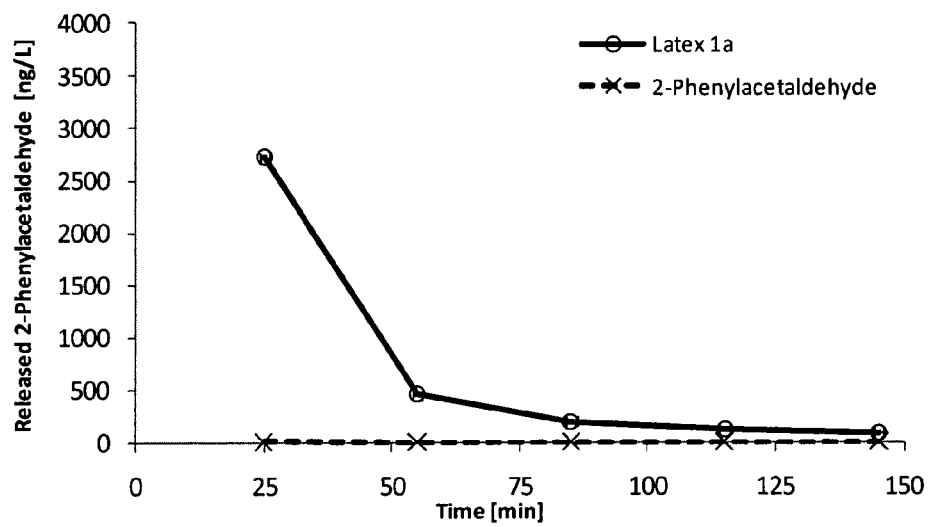
(b)
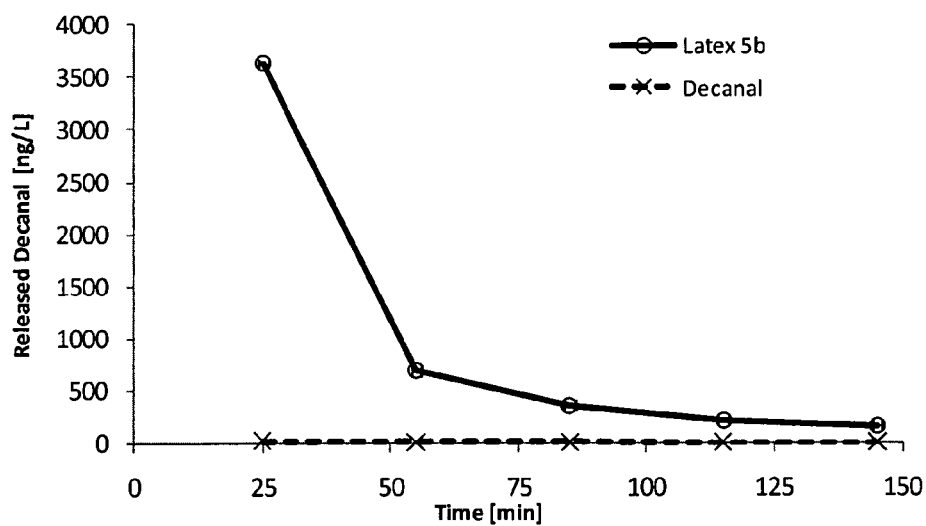

Figure 8:   Decomposition reaction
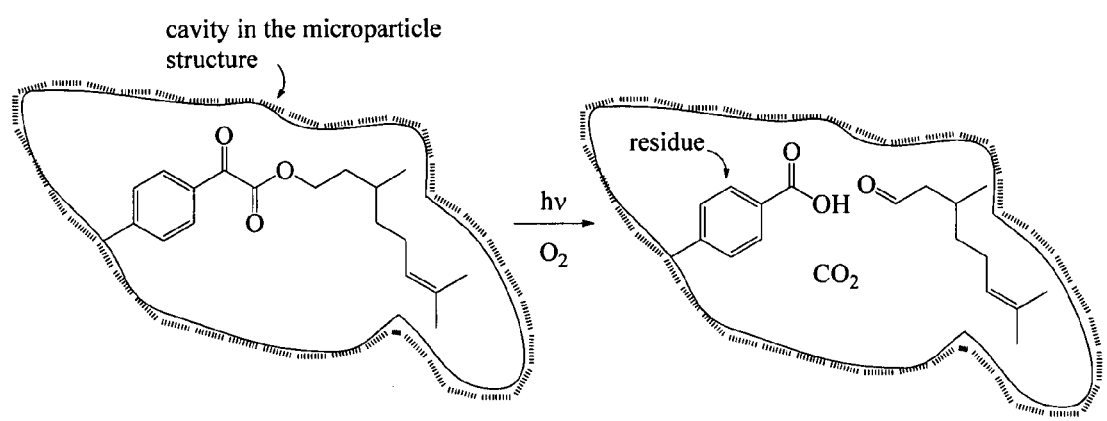

PHOTOLABILE LATEX FOR THE RELEASE OF PERFUMES

This application is a 371 filing of International Patent Application PCT/EP2012/069208 filed Sep. 28, 2012, which claims the benefit of European patent application no. 11184210.0 filed Oct. 6, 2011.

TECHNICAL FIELD

The present invention relates to the field of perfumery. More particularly, it concerns co-polymeric latex particles derived from 2-oxo-2-(3- or 4-vinylphenyl)acetates capable of liberating an active molecule such as, for example, an aldehyde or ketone upon exposure to light. The present invention also concerns the use of said latex in perfumery, as well as the perfuming compositions or perfumed articles comprising the invention's latex.

PRIOR ART

The perfume industry has a particular interest for derivatives which are capable of prolonging the effect of active ingredients over a certain period of time, for example in order to overcome the problems encountered when using perfuming ingredients which are too volatile or have a poor substantivity. In particular, the industry is interested by derivatives capable of performing an improved olfactive performance. Said improvement can be in time, in intensity or in the effective amount of active compound released.

The patent application WO 99/60990 describes a class of 2-oxo-2-phenylacetates capable of releasing perfuming aldehydes or ketones upon exposure to light and thus prolonging the effect of the perfuming ingredients as such. However, although said prior art compounds have shown a number of promising behaviors in laboratory tests, in real applications they have shown to be of very limited interest, since they suffer of chemical instability due to a premature solvolysis (hydrolysis) of the ester moiety which significantly affects the performance in different consumer products.

For long the industry has tried to find a system that allows keeping the advantages of the prior art compounds and solving the problem of stability.

Despite all the disadvantages one might reasonably expect from the use of non-hollow microcapsules and latexes, such as unfavorable transparency to visible light or reduced rates of diffusion of the released material into the air through compact organic particles (which should retain the perfuming ingredients) etc., we surprisingly found that the co-polymeric latex particles of the invention solve the above mentioned problems and can also be used as effective perfuming ingredients.

The invention's co-polymers are believed to have never been specifically disclosed or suggested in the prior art, nor their particular performances in the field of perfume release.

DESCRIPTION OF THE INVENTION

We have now surprisingly discovered the existence of specific polymer microparticles, derived from 2-oxo-2-(3- or 4-vinylphenyl)acetates and a cross-linking monomer, which are capable of liberating a perfuming aldehyde or ketone upon light irradiation and which provide superior performances compared to the existing photo-releasing systems. By "perfuming aldehyde or ketone" we mean here any aldehyde or ketone capable of bringing an odor benefit or effect into its surrounding environment. Said particles can be obtained in the form of latex, wherein by "latex" we mean here the classical meaning, e.g. a stable colloidal dispersion or emulsion of polymer microparticles in an aqueous or alcoholic medium. Said polymer microparticles are not-hollow, and are preferably essentially spherical. By the expression "not-hollow" it is meant that the interior of such microparticles is made/filled of the same material as exterior of such microparticles, i.e. they are not of the core-shell type.

Said polymer microparticles, or the corresponding latexes, can be used as perfuming ingredients.

A first object of the present invention concerns a polymer microparticle, derived from 2-oxo-2-(3- or 4-vinylphenyl) acetates, capable of releasing in a controlled manner a perfuming aldehyde or ketone, said polymer microparticle comprising a) at least one repeating unit of formula

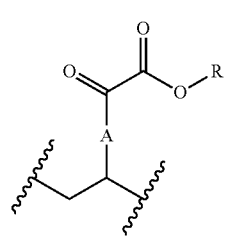

(I)

wherein A represents a benzene-1,4-diyl or a benzene-1,3-diyl moiety, and R is a CH(R')(R") group corresponding to a $C_{6-20}$ perfuming aldehyde (i.e. R' is H) or ketone of formula (R')(R")C=O;

b) optionally at least one repeating cross-linking unit of formula

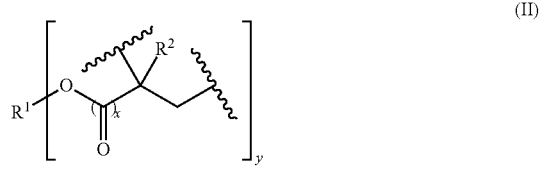

(II)

wherein all x are simultaneously either 0 or 1, y is 2, 3 or 4; $R^1$ represents a $C_{2-12}$ hydrocarbon di-, tri- or tetra-radical (depending on the value of y) optionally comprising from 1 to 5 oxygen atoms; and $R^2$ represents a hydrogen atom or a methyl group;

alternatively, the repeating cross-linking unit is of formula

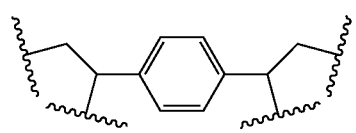

(III)

c) optionally at least one repeating unit of the formulae

(IV-a)

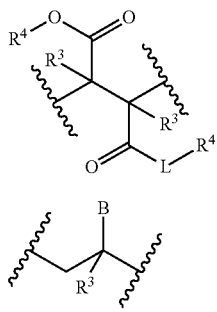
(IV-b)

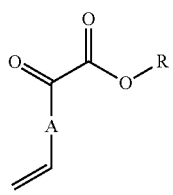
(IV-c)

wherein L is an oxygen atom or a NH group, B represents a COOR⁴ group, a C₆H₅, a C₆H₄COOR⁴, a OR⁴, a R⁴COO, a CON(R⁴)₂, or a 2-oxopyrrolidin-1-yl or a 2-oxoazepan-1-yl group and each R³ is a hydrogen atom or a methyl group, and each R⁴ represents a hydrogen atom, a C₁₋₄ alkyl group or a (C₂H₄O)$_q$R³ group, with q being an integer varying between 1 and 10;

provided that at least 2% w/w of the whole repeating unit of formula (I) are units wherein R is a CH(R')(R") group corresponding to a C₆₋₂₀ perfuming aldehyde or ketone of formula (R')(R")C=O.

Said polymer microparticle is obtainable by a process comprising the steps of:

1) preparing a solution, dispersion or emulsion of:
   at least one monomer of formula

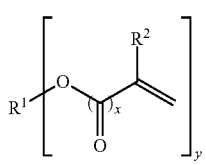
(I')

wherein A and R have the meaning indicated in formula (I);

optionally at least one cross-linking monomer of formula

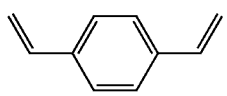
(II')

wherein x, y, R¹ and R² have the meaning indicated in formula (II);

or of formula (III')

optionally at least one monomer of the formulae

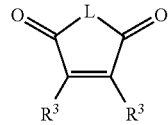
(IV-a')

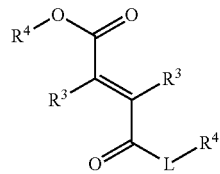
(IV-b')

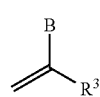
(IV-c')

wherein L, R³, R⁴ and B have the meaning indicated in formulae (IV-a), (IV-b), (IV-c);

provided that at least 2% w/w of the whole monomer of formula (I) is a monomer wherein R is a CH(R')(R") group corresponding to a C₆₋₂₀ perfuming aldehyde or ketone of formula (R')(R")C=O;

in a water- or lower alcohol-based medium, or in an organic solvent having a solubility parameter between 15 and 25 (MPa)$^{0.5}$; and 2) promoting the polymerization (this step providing a latex, a dispersion or a solution), and, 3) optionally, isolating the polymer as a microparticle as such in a dry form.

Non limiting examples of organic solvents which can be used to prepare the polymer of the present invention in solution comprise tetrahydrofuran, ethyl acetate, cyclohexane, dioxane, pyridine, acetone, benzene, chloroform, or toluene.

The resulting polymer prepared in an organic solvent, once dried, can be converted into a latex to be used in the final product.

The group R is defined above as being derived from a perfuming aldehyde or ketone. An exhaustive list of said perfuming aldehydes or ketones would be too long and tedious to be given, however a person skilled in the art of perfumery knows exactly what means and encompasses the expression "perfuming aldehyde or ketone". For example one may make reference to the definition provided further below when "perfuming co-ingredient" is mentioned. Furthermore, it is useful to emphasize the fact that the perfuming aldehyde or ketone in compound (I) is present in the form of its corresponding primary or secondary alcohol (R')(R")CH—OH, this is due to the specific mechanism of release which is exemplified further below. These primary or secondary alcohols can be obtained by reduction of the corresponding aldehydes or ketones, respectively, e.g. by reaction with LiAlH₄.

Indeed, upon exposure to the light, and in the presence of oxygen, the repeating units of formula (I) undergo the following fragmentation:

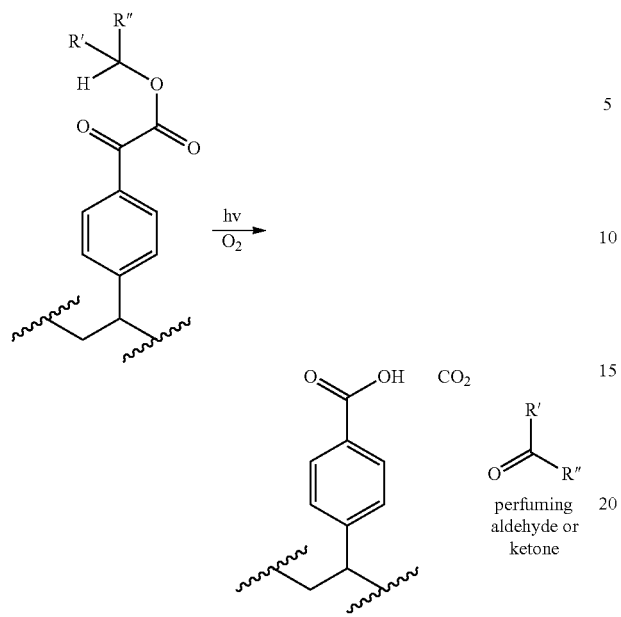

wherein the moiety (R')(R")CH—O (i.e. OR) is transformed into the perfuming aldehyde or ketone (R')(R")C=O. The photofragmentation mechanism is believed to be a photooxidation as generally described in the literature for 2-oxoacetates involving abstraction of the hydrogen from the (R')(R")CH—O moiety onto the 2-oxo group of the keto ester group as one of the key steps. Therefore, and for the sake of clarity, when the perfuming aldehyde (R')(R")C=O is e.g. citronellal, the corresponding alcohol (R')(R")CH—OH is citronellol and R is citronellyl. Similarly, when the perfuming ketone (R')(R")C=O is e.g. 2,5-dimethyl-2-octene-6-one, the corresponding alcohol (R')(R")CH—OH is 2,5-dimethyl-2-octene-6-ol and R is 2,5-dimethyl-2-octene-6-yl.

According to any one of the embodiments of the invention, said R is a CH(R')(R") group corresponding to a $C_{6-15}$ perfuming aldehyde or ketone of formula (R')(R")C=O.

Examples of such aldehydes or ketones are provided in the literature, such as the patent literature or dedicated books (e.g. see the book by S. Arctander, Perfume and Flavor Chemicals, 1969, Montclair, N.J., USA, or its more recent versions) and are well known to a person skilled in the art.

According to any one of the embodiments of the invention, said and R is a CH(R')(R") group corresponding to a perfuming:
  aldehyde, such as benzaldehyde, 1,3-benzodioxol-5-carboxaldehyde (heliotropine), 3-(1,3-benzodioxol-5-yl)-2-methylpropanal, 3-(4-tert-butyl-1-cyclohexen-1-yl)propanal (Mugoxal®, origin: Firmenich SA, Geneva, Switzerland), 2,4-decadienal, 2-decenal, 4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde (Triplal®, origin: International Flavors & Fragrances, New York, USA), 3,5-dimethyl-3-cyclohexene-1-carbaldehyde, 1-(3,3-dimethyl-1-cyclohexyl)-1-ethanone, 5,9-dimethyl-4,8-decadienal, 3-(3,3- and 1,1-dimethyl-2,3-dihydro-1H-inden-5-yl)propanal, 2,6-dimethyl-5-heptenal (melonal), 3,7-dimethyl-2,6-octadienal (citral), 3,7-dimethyloctanal, 3,7-dimethyl-6-octenal (citronellal), (3,7-dimethyl-6-octenyl)acetaldehyde, 3-dodecenal, 4-dodecenal, 3-ethoxy-4-hydroxybenzaldehyde (ethyl vanillin), 4-ethyl benzaldehyde, 3-(2 and 4-ethylphenyl)-2,2-dimethylpropanal, 2-furancarbaldehyde (furfural), 2,4-heptadienal, 3,5,5,6,7,8,8-heptamethyl-5,6,7,8-tetrahydronaphthalene-2-carbaldehyde (Vulcanolide®, origin: Firmenich SA, Geneva, Switzerland), 4-heptenal, 2-hexenal, 3-hexenal, 2-hexyl-3-phenyl-2-propenal (hexylcinnamic aldehyde), 2-hydroxybenzaldehyde, 7-hydroxy-3,7-dimethyloctanal (hydroxycitronellal), 4-hydroxy-3-methoxybenzaldehyde (vanillin), 4- and 3-(4-hydroxy-4-methylpentyl)-3-cyclohexene-1-carbaldehyde (Lyral®, origin: International Flavors and Fragrances, New York, USA), 4-isopropylbenzaldehyde (cuminaldehyde), 8-isopropyl-6-methyl-bicyclo[2.2.2]oct-5-ene-2-carbaldehyde, 3-(4-isopropylphenyl)-2-methylpropanal, 2-(4-isopropylphenyl)propanal, 2- and 4-methoxybenzaldehyde (anis aldehyde), 6-methoxy-2,6-dimethylheptanal (methoxymelonal), 3-(2-methoxyphenyl)acrylaldehyde, 8(9)-methoxy-tricyclo[5.2.1.0.(2,6)]decane-3(4)-carbaldehyde (Scentenal®, origin: Firmenich SA, Geneva, Switzerland), 4-methylbenzaldehyde, 3-(4-methylcyclohex-3-en-1-yl)butanal (Liminal®, origin: Firmenich SA, Geneva, Switzerland), 2-(4-methylenecyclohexyl)propanal, 1-methyl-4-(4-methyl-3-pentenyl)-3-cyclohexen-1-carbaldehyde (Precyclemone® B, origin: International Flavors & Fragrances, New York, USA), 3-(4-methyl-3-pentenyl)-3-cyclohexene-1-carbaldehyde, 4-(4-methyl-3-pentenyl)-3-cyclohexene-1-carbaldehyde (Acropal®, origin: Givaudan-Roure SA., Vernier, Switzerland), (4-methylphenoxy)acetaldehyde, (4-methylphenyl) acetaldehyde, 3-methyl-5-phenylpentanal (Phenexal®, origin: Firmenich SA, Geneva, Switzerland), 2-(1-methylpropyl)-1-cyclohexanone, 2-methyl-4-(2',2',3'-trimethyl-3'-cyclopentenyl)-4-pentenal, 2,4-nonadienal, 2,6-nonadienal, 2-nonenal, 3-nonenal, 6-nonenal, 8-nonenal, 2-octenal, 2-pentyl-3-phenyl-2-propenal, phenoxyacetaldehyde, 2-phenylacetaldehyde, 3-phenylbutanal (Trifernal®, origin: Firmenich SA, Geneva, Switzerland), 3-phenylpropanal, 2-phenylpropanal (hydratropaldehyde), 3-phenyl-2-propenal (cinnamic aldehyde), 4-(prop-1-en-2-yl)cyclohex-1-enecarbaldehyde (perillaldehyde), 3-(4-tert-butylphenyl)-2-methylpropanal (Lilial®, origin: Givaudan-Roure SA, Vernier, Switzerland), 3-(4-tert-butylphenyl)propanal (Bourgeonal®, origin: Quest International, Naarden, Netherlands), tricyclo[5.2.1.0(2,6)]decane-4-carbaldehyde, exo-tricyclo[5.2.1.0(2,6)]decane-8exo-carbaldehyde (Vertral®, origin: Symrise, Holzminden, Germany), 2,6,6-trimethyl-bicyclo[3.1.1]heptane-3-carbaldehyde (formyl pinane), 2,4,6- and 3,5,6-trimethyl-3-cyclohexene-1-carbaldehyde, 2,2,3-trimethyl-3-cyclopentene-1-acetaldehyde (campholenic aldehyde), 2,6,10-trimethyl-2,6,9,11-dodecatetraenal, 2,5,6-trimethyl-4-heptenal, 3,5,5-trimethylhexanal, 2,6,10-trimethyl-9-undecenal, 2-undecenal, 10-undecenal or 9-undecenal and their mixtures such as Intreleven aldehyde (origin: International Flavors & Fragrances, New York, USA) or Aldehyde Supra (origin: Firmenich SA, Geneva, Switzerland), an aldehyde of formula (R")CHO wherein R" is a linear or α-branched alkyl group of $C_6$ to $C_{15}$, or
  ketone, such as a damascenone, a damascone, a ionone or methyl ionone (such as Iralia® Total, origin: Firmenich SA, Geneva, Switzerland), irone, macrocyclic ketone such as, for example, cyclopentadecanone (Exaltone®) or 3-methyl-4-cyclopentadecen-1-one and 3-methyl-5-cyclopentadecen-1-one (Delta Muscenone) or 3-methyl-1-cyclopentadecanone (Muscone) all from Firmenich SA, Geneva, Switzerland, 1-(2-aminophenyl)-1-ethanone, 1-(3,3-dimethyl-1-cyclohexen-1-yl)-4-penten-1-one, 1-(5,5-dimethyl-1-cyclohexen-1-yl)-4-penten-1-one (Neobutenone®, origin: Firmenich SA, Geneva, Switzerland), 1-(3,3-dimethyl-1-cyclohexyl)-1-ethanone, 2,5-dimethyl-2-octene-6-one, 4,7-dimethyl-6-octene-3-one, (3,7-dimethyl-6-octenyloxy)acetaldehyde, 1-(2,4-dimethylphenyl)-1-ethanone, 4-(1,1-dimethylpropyl)-1-cyclohexanone (Orivone®, origin: International Flavors & Fragrances, New York, USA), 2,4-di-tert-butyl-1-cyclohexanone, ethyl 4-oxopentanoate, 1-(4-ethylphenyl)-1-ethanone, 1-(3,5,5,6,8,8-hexamethyl-5,6,7,8-tetrahydronaphthalen-2-yl)ethanone (Fixolide®, origin: Givaudan-Roure SA, Vernier, Switzerland), 2-hexyl-1-cyclopentanone, 2-hydroxy-3-methyl-2-cyclopenten-1-one, 4-(4-hydroxy-1-phenyl)-2-butanone (raspberry ketone), 1-(2- and 4-hydroxyphenyl)-1-ethanone, 2-isopropyl-5-methylcyclohexanone (menthone), 4-isopropyl-2-cyclohexen-1-one, 1-(5-isopropyl-2-methylcyclohex-1- or 2-en-1-yl)propanone, 1-(4-isopropyl-1-phenyl)-1-ethanone, 2-(2-mercaptopropan-2-yl)-5-methylcyclohexanone, 1-(4-methoxyphenyl)-1-ethanone, 7-methyl-2H,4H-1,5-benzodioxepin-3-one (Calone®, origin: C.A.L. SA, Grasse, France), 5-methyl-3-heptanone, 6-methyl-5-hepten-2-one, methyl 3-oxo-2-pentyl-1-cyclopentaneacetate (Hedione®, origin: Firmenich SA, Geneva, Switzerland), 1-(4-methylphenyl)-1-ethanone (4-methylacetophenone), 5-methyl-2-(propan-2-ylidene)cyclohexanone, 5-methyl-2-(prop-1-en-2-yl)cyclohexanone (isopulegone), 2-methyl-5-(prop-1-en-2-yl)cyclohex-2-enone (carvone), 5-methyl-exo-tricyclo[6.2.1.0(2,7)]undecan-4-one, 3-methyl-4-(1,2,2-trimethylpropyl)-4-penten-2-one, 2-naphthalenyl-1-ethanone, 1-(octahydro-2,3,8,8-tetrame-2-naphthalenyl)-1-ethanone (isomeric mixture, Iso E Super®, origin: International Flavors & Fragrances, New York, USA), 3,4,5,6,6-pentamethyl-3-hepten-2-one, 2-pentyl-1-cyclopentanone (Delphone, origin: Firmenich SA, Geneva, Switzerland), 4-phenyl-2-butanone (benzylacetone), 1-phenyl-1-ethanone (acetophenone), 2- and 4-tert-butyl-1-cyclohexanone, 1-(4-tert-butylphenyl)-1-ethanone), 3,5,6,6-tetramethyl-4-methyleneheptan-2-one, 2,4,4,7-tetramethyl-6-octen-3-one, 1,7,7-trimethyl-bicyclo[2.2.1]heptan-2-one (camphor), 2,6,6-trimethyl-1-cycloheptanone, 2,6,6-trimethyl-2-cyclohexene-1,4-dione, 4-(2,6,6-trimethyl-2-cyclohexen-1-yl)-2-butanone (dihydroionone), 1-(2,4,4-trimethyl-2-cyclohexen-1-yl)-2-buten-1-one, 1-(3,5,6-trimethyl-3-cyclohexen-1-yl)-1-ethanone, 2,2,5-trimethyl-5-pentyl-1-cyclopentanone or a $C_{6-15}$ ketone of formula (R')(R")C=O wherein R' and R" are linear alkyl groups.

According to any one of the embodiments of the invention, said A represents a benzene-1,4-diyl group, i.e. the compound of formula (I) is a derivative of 2-oxo-2-(4-vinylphenyl)acetic acid.

According to any one of the embodiments of the invention, the polymer microparticles contain at least one repeating cross-linking unit of formula (II).

According to any one of the embodiments of the invention, said $R^1$ represents a $C_{2-9}$ hydrocarbon di-, tri- or tetra-radical (depending on the value of y) optionally comprising 1, 2, 3 or 4 oxygen atoms. For the sake of clarity, in the present invention by "comprising . . . oxygen atoms" it is meant that said atoms are part of functional groups like ketones, ethers, esters or alcohols.

According to any one of the embodiments of the invention, said $R^1$ in formula (II) represents a di, tri- or tetra radical of formulae

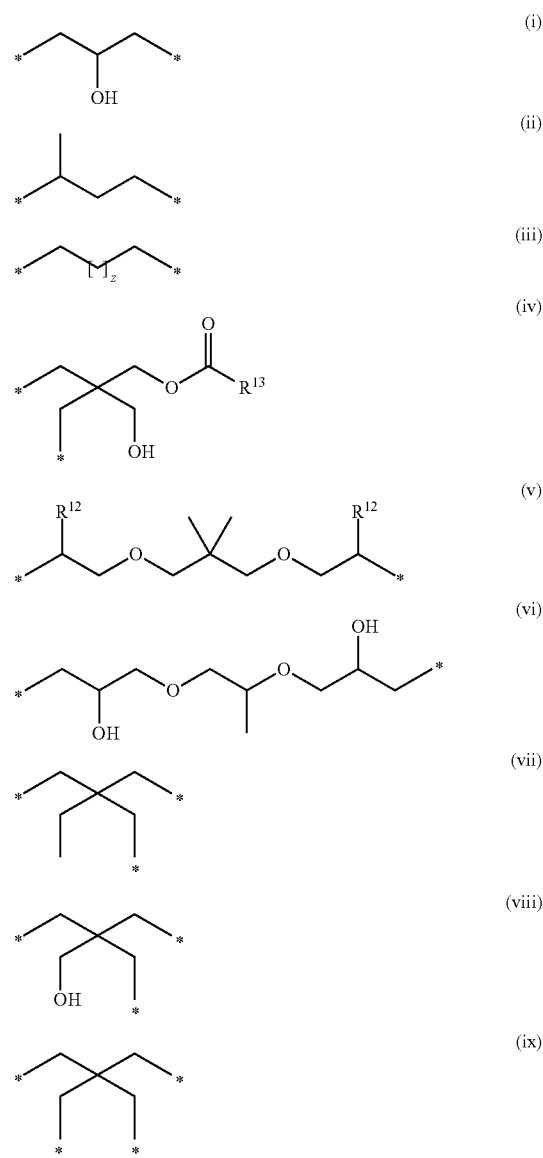

wherein the asterisk marks the link to the oxygen atom in formula (II); z is an integer varying between 0 and 4, $R^{12}$ is a hydrogen atom or a methyl group, and $R^{13}$ is a $C_{1-4}$ linear hydrocarbon chain.

According to any one of the embodiments of the invention, said $R^2$ represents a hydrogen atom.

According to any one of the embodiments of the invention, said $R^3$ represents a hydrogen atom.

According to any one of the embodiments of the invention, said $R^4$ represents a hydrogen atom or a methyl, ethyl, propyl, isopropyl or butyl group.

According to any one of the embodiments of the invention, said x is 1.

According to any one of the embodiments of the invention, said y is 2 or 3.

The invention's latex or polymer microparticle may also comprise another repeating unit of formula (IV). According to any one of the embodiments of the invention, said B represents a COOH, a COOCH$_3$, a C$_6$H$_5$, a C$_6$H$_4$COOH, a OH, a CH$_3$COO, a CONH$_2$, or a 2-oxopyrrolidin-1-yl or a 2-oxoazepan-1-yl group.

According to any one of the embodiments of the invention, said L represents an oxygen atom.

According to any one of the embodiments of the invention, the monomers of formula (I') are in particular decyl 2-oxo-2-(4-vinylphenyl)acetate, 3,7-dimethylocta-2,6-dien-1-yl 2-oxo-2-(4-vinylphenyl)acetate, 3,7-dimethyloct-6-en-1-yl 2-oxo-2-(4-vinylphenyl)acetate, 3,7-dimethyloctyl 2-oxo-2-(4-vinylphenyl)acetate, 2-isopropyl-5-methylcyclohexyl 2-oxo-2-(4-vinylphenyl)acetate, hex-3-en-1-yl 2-oxo-2-(4-vinylphenyl)acetate, 2-phenylethyl 2-oxo-2-(4-vinylphenyl)acetate, 3-methyl-5-phenylpentyl 2-oxo-2-(4-vinylphenyl)acetate or 4-(2,6,6-trimethylcyclohex-1- or 2-en-1-yl)but-3-en-2-yl 2-oxo-2-(4-vinylphenyl)acetate. It is understood that according to said embodiments the repeating units of formula (I) are those corresponding to said monomers.

According to any one of the embodiments of the invention, the monomers of formula (II') are in particular 1,4-butanediol divinyl ether, ethane-1,2-diyl diacrylate, propane-1,3-diyl diacrylate, butane-1,4-diyl diacrylate, hexane-1,6-diyl diacrylate, ((2,2-dimethylpropane-1,3-diyl)bis(oxy))bis(propane-2,1-diyl)diacrylate, 2-((acryloyloxy)methyl)-2-(hydroxymethyl)propane-1,3-diyl diacrylate, 2,2-bis((acryloyloxy)methyl)propane-1,3-diyl diacrylate, 2-((acryloyloxy)methyl)-2-ethylpropane-1,3-diyl diacrylate. It is understood that according to said embodiments the repeating units of formula (II) are those corresponding to said monomers.

According to any one of the embodiments of the invention, the monomers of formula (IV-a') are in particular maleic anhydride or maleimide. It is understood that according to said embodiments the repeating units of formula (IV-a) are those corresponding to said monomers.

According to any one of the embodiments of the invention, the monomers of formula (IV-b') are in particular isopropyl, ethyl or methyl maleate mono- or diester or maleic acid. It is understood that according to said embodiments the repeating units of formula (IV-b) are those corresponding to said monomers.

According to any one of the embodiments of the invention, the monomers of formula (IV-c') are in particular styrene, methyl methacrylate, ethyl methacrylate, n-butyl methacrylate, methyl acrylate, ethyl acrylate, n-butyl acrylate, N-vinylpyrrolidinone, vinyl acetate, vinyl alcohol, N-vinylcaprolactame, acrylamide, methacrylamide. It is understood that according to said embodiments the repeating units of formula (IV-c) are those corresponding to said monomers (e.g. if the compound (IV-c') is styrene then the unit (IV-c) is a 1-phenylethane-1,2-diyl moiety).

The invention's polymer microparticle may be made of a random co-polymer or of a block co-polymer. According to any one of the embodiments of the invention, the co-polymer is preferentially of the random, or statistic, type.

Furthermore, according to another embodiment of the invention, the invention's polymer microparticle may be characterized by an average size of the particle comprised in the range between 100 nm and 100 μm, more particularly between 0.2 μm and 20 μm.

According to any one of the embodiments of the invention, the invention's polymer microparticles are characterized by a repeating unit (I) wherein the corresponding monomer (I') has a Hansen solubility parameter comprised between 15 and 25 (MPa)$^{0.5}$.

According to any one of the embodiments of the invention, the invention's polymer microparticles are characterized by a repeating unit (II) or (III) wherein the corresponding monomer (II') or (III') has a Hansen solubility parameter comprised between 10 and 29 (MPa)$^{0.5}$.

According to any one of the embodiments of the invention, the invention's polymer microparticles are characterized by a repeating unit (IV-a), (IV-b) or (IV-c) wherein the corresponding monomer (IV-a'), (IV-b') or (IV-c') has a Hansen solubility parameter comprised between 15 and 29 (MPa)$^{0.5}$.

For the sake of clarity the "Hansen solubility parameter" is defined as the square root of the cohesive energy density, obtained according to the method of Marrero and Gani using the ICAS 13.0, ProPred Component Property Prediction software (Marrero and Gani, "Group-Contribution Based Estimation of Pure Component Properties", Fluid Phase Equilibria, 183-184 (2001) 183-208).

The following table lists the Hansen solubility parameters δ for a series of monomers, co-monomers and fragrance aldehydes and ketones.

| Monomers according to the invention | Hansen solubility parameter δ (MPa$^{0.5}$)[a] |
|---|---|
| Methyl methacrylate | 17.60 |
| Methyl acrylate | 18.40 |
| Methacrylic acid | 20.94 |
| Acrylic acid | 21.78 |
| Styrene | 19.44 |
| 4-Vinylbenzoic acid | 20.68 |
| Vinyl acetate | 18.25 |
| N-vinyl pyrrolidinone | 22.39 |
| n-Butyl Methacrylate | 16.99 |
| n-Butyl Acrylate | 17.73 |
| Maleic Anhydride | 25.03 |
| Maleic Acid | 28.23 |
| (Z)-Hex-3-en-1-yl 2-oxo-2-(4-vinylphenyl)acetate | 21.07 |
| 3,7-Dimethylocta-2,6-dien-1-yl 2-oxo-2-(4-vinylphenyl)acetate | 21.41 |
| 2-Phenylethyl 2-oxo-2-(4-vinylphenyl)acetate | 23.66 |
| (1R,2S,5R)-2-Isopropyl-5-methylcyclohexyl 2-oxo-2-(4-vinylphenyl)acetate | 22.22 |
| Decyl 2-oxo-2-(4-vinylphenyl)acetate | 20.40 |

[a]Data obtained according to the method of Marrero and Gani using the ICAS 13.0, ProPred Component Property Prediction software.

According to any one of the embodiments of the invention, the perfuming aldehyde or ketone (R')(R")C=O has a Hansen solubility parameter between 15 and 28 MPa$^{0.5}$.

The following table lists the Hansen solubility parameters δ for a series of monomers, co-monomers and fragrance aldehydes and ketones.

| Fragrance aldehydes and ketones and some solvents | Hansen solubility parameter δ (MPa$^{0.5}$) |
|---|---|
| Water | 47.9[b] |
| Ethanol | 26.2[a] |
| Acetone | 20.3[a] |
| (Z)-Hex-3-enal | 18.95[a] |
| Citral | 20.34[a] |
| 2-Phenylacetaldehyde | 21.28[a] |
| Menthone | 16.81[a] |
| Decanal | 17.91[a] |

[a]Data obtained according to the method of Marrero and Gani using ICAS 13.0, ProPred Component Property Prediction software;
[b]Data obtained from Sheehan and Bisio, Rubber Chemistry and Technology, 1966, 39(1), 149-192.

The invention's polymer microparticles, characterized by the above described solubility parameters, are particularly suitable since we found that they unexpectedly combine an appropriate hydrophobicity to prevent hydrolysis problems with an appropriate hydrophilicity to allow an effective release of the liberated perfuming aldehyde or ketone.

Specifically, each molecule is characterized by three Hansen parameters, which are generally expressed in MPa$^{0.5}$:

$\delta_d$: represents the energy from dispersion forces between molecules;

$\delta_p$: represents the energy from dipolar intermolecular forces between molecules;

$\delta_h$: represents the energy from hydrogen bonds between molecules;

and the value of the Hansen solubility parameter is obtained by the formula:

$$\delta = (\delta_d^2 + \delta_p^2 + \delta_h^2)^{0.5}.$$

The Hansen solubility parameter of a co-polymer is calculated from the Hansen solubility parameters of the corresponding monomers by taking into account the mole fraction of each monomer in the final co-polymer.

As an example, the co-polymer prepared in Example 1 consists of 70 mol % of methyl methacrylate ($\delta=17.60$ MPa$^{0.5}$, see Table) and 30 mol % of 2-phenylethyl 2-oxo-2-(4-vinylphenyl)acetate ($\delta=23.66$ MPa$^{0.5}$). Neglecting the cross-linker (0.1%), the final co-polymer has a Hansen solubility parameter of 19.42 MPa$^{0.5}$. Upon exposure to daylight, the fragrance is released, forming a new monomer unit (4-vinylbenzoic acid, $\delta=20.68$ MPa$^{0.5}$) in the co-polymer. The resulting co-polymer has (after quantitative fragrance release) a Hansen solubility parameter of 18.52 MPa$^{0.5}$. The Hansen solubility parameter of the released fragrance (2-phenylacetaldehyde, $\delta=21.28$ MPa$^{0.5}$) is much closer to that of the remaining co-polymer ($\delta=18.52$ MPa$^{0.5}$) than to that of water ($\delta=47.9$ MPa$^{0.5}$) and is therefore considerably more compatible with the co-polymer than with its local environment. Therefore one would expect that the fragrance will preferentially remain sorbed to the co-polymer particles rather than being released into the environment. Based on these reflections, it is surprising to observe an efficient release of a fragrance with a Hansen solubility parameter varying between 15 and 28 MPa$^{0.5}$ from a polymer microparticle according to the present invention with a Hansen solubility parameter varying between 10 and 29 MPa$^{0.5}$.

Furthermore, it is also useful to mention that according to any one of the embodiments of the invention the molar ratio between the total amount of the repeating unit (I) and the total amount of repeating units of the invention's co-polymers (hereinafter (I)/(Tot)) can be comprised between 1/100 and 100/100, and in particular between 5/100 and 100/100, or even between 20/100 and 100/100 (it is understood that said ranges are applicable to the monomers used in the process for the preparation of the polymer microparticle).

Furthermore, it is also useful to mention that according to any one of the embodiments of the invention the molar ratio between the total amount of the repeating unit (II) and the total amount of repeating units of the invention's co-polymers (hereinafter (II)/(Tot)) can be comprised between 0/100 and 99.9/100, and in particular between 0.02/100 and 10/100, or even between 0.05/100 and 2/100 (it is understood that said ranges are applicable to the monomers used in the process for the preparation of the polymer microparticle).

Furthermore, it is also useful to mention that the according to any one of the embodiments of the invention molar ratio between the total amount of the repeating unit (IV-c) and the total amount of repeating units of the invention's co-polymers (hereinafter (IV-c)/(Tot)) can be comprised between 0 and 99/100, and in particular between 5/100 and 98/100, or even between 25/100 and 96/100 (it is understood that said ranges are applicable to the monomers used in the process for the preparation of the polymer microparticle).

As mentioned above the invention's polymer microparticle can be obtained by a three step process.

For the sake of clarity, by the expression "water- or lower alcohol-based medium" it is meant here a liquid medium comprising at least 80%, or even 90%, 95% or 100%, w/w of its weight of water or a $C_{1-4}$ alkanol or mixtures thereof. Said medium may comprise up to 5%, 10% or 20%, w/w of its weight of other solvents which are totally miscible with water.

According to any one of the embodiments of the invention, the dispersion or emulsion can be obtained as an emulsion, a dispersion or a solution in water, methanol, or ethanol, or mixtures thereof.

According to any one of the embodiments of the invention, the dispersion or emulsion may further comprise a colloidal stabilizer, such as poly(vinyl alcohol), poly(vinyl alcohol-co-acrylic acid), or poly(N-vinyl pyrrolidinone) and co-polymers thereof.

According to any one of the embodiments of the invention, the polymerization can be initiated by 2,2'-azobis(2-methylpropionitrile) (AIBN), dibenzoyle peroxide, 2,2'-azobis(2-methylpropionamidine)dihydrochloride, 2,2'-azobis[N-(2-carboxyethyl)-2-methylpropionamidine]hydrate (VA-057), ammonium persulfate, sodium persulfate, potassium persulfate. 2,2'-azobis(2,4-dimethylvaleronitrile) (VAZO®-52).

According to any one of the embodiments of the invention, the isolation in a dry form is achieved by filtration, solvent evaporation or spray-drying.

Owing to their particular chemical structure the invention's polymers or co-polymers are capable of releasing, via a light-induced decomposition reaction, a residue and a perfuming aldehyde or ketone, as shown in FIG. 8 wherein only one repeating unit is shown.

The perfuming aldehyde or ketone still needs to diffuse out of the structure of the microparticle at an appropriate rate in order to be released into the surrounding air, and to be perceived and deliver the desired effect.

As mentioned above, to synthesize the invention's polymer microparticle it is necessary to use as starting material a monomer of formula (I). Said compound is novel over the prior art and is also a further object of the present invention as essential precursor of the invention's polymer microparticle.

2-Oxo-2-phenylacetate based monomers of formula (I) can, as non-limiting examples, be prepared by transesterification of methyl or ethyl 2-oxo-2-(4-vinylphenyl)acetate with a primary or secondary alcohol of formula (R')(R'')CH—OH, or by Grignard reaction of 3- or 4-bromostyrene with dialkyl oxalates previously obtained by reaction of oxalyl chloride with a primary or secondary alcohol of formula (R')(R'')CH—OH.

In all aspects of the above-described invention, the invention's polymer microparticle might be used in the presence of other fragrance delivery systems, in particular in the presence of other light-sensitive fragrance delivery systems, such as the 2-oxoacetates mentioned in WO 99/60990, or even in the presence of other delivery systems having a complementary release profile.

As mentioned above, the invention concerns the use of the above-described polymer microparticle, or latex, as perfuming ingredient. In other words it concerns a method to confer, enhance, improve or modify the odor properties of a perfuming composition or of a perfumed article, which method comprises adding to said composition or article an effective amount of at least a polymer microparticle, or latex, according to the invention. By "use of an invention's polymer microparticle, or latex," it has to be understood here also the use of any composition containing said polymer microparticle, or latex, and which can be advantageously employed in perfumery industry as active ingredient.

Said compositions, which in fact can be advantageously employed as perfuming ingredient, are also an object of the present invention.

Therefore, another object of the present invention is a perfuming composition comprising:
i) as perfuming ingredient, at least one invention's polymer microparticle, or latex, as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carriers one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can also be water, ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

By "perfumery base" we mean here a composition comprising at least one perfuming co-ingredient.

Said perfuming co-ingredient is not an invention's latex. Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds (fragrance precursors or core-shell capsules containing a perfume).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one latex and at least one perfumery carrier represents a particular embodiment of the invention as well as a perfuming composition comprising at least one latex, at least one perfumery carrier, at least one perfumery base, and optionally at least one perfumery adjuvant.

It is useful to mention here that the possibility of having, in the compositions mentioned above, more than one of the invention's co-polymers is important as it enables the perfumer to prepare accords, perfumes, possessing the odor tonality of various compounds of the invention, creating thus new tools for their work.

Furthermore, an invention's latex, or a perfuming composition comprising it, is a useful perfuming ingredient, which can be advantageously used in all the fields of modern perfumery, such as fine perfumery or functional perfumery. Indeed, the invention's latex may be advantageously employed in fine or functional perfumery to achieve a more controlled deposition, and consequent release, of odoriferous compounds. For example, the latex according to the invention, owing to a well controlled release of odoriferous molecules, can be incorporated in any application requiring the effect of rapid or prolonged liberation of an odoriferous component as defined hereinabove and furthermore can impart a fragrance and a freshness to a treated surface which will last well beyond the rinsing and/or drying processes. Suitable surfaces are, in particular, textiles, hard surfaces, hair and skin.

Consequently, a perfuming consumer product which comprises:
i) as perfuming ingredient, at least one polymer microparticle, or latex, as defined above; and
ii) a perfumery consumer base;
is also an object of the present invention.

The invention's latex can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface).

In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of a suitable perfumery consumer base can be a perfume, such as a fine fragrance, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, cream, shower or bath mousse, oil or gel, or a hygiene product); an air care product, such as an air freshener or a "ready to use" powdered air freshener; or a home care product, such as a wipe, a dish detergent or hard-surface detergent.

As anticipated above, the invention's composition can be advantageously used for bringing a benefit to consumer products, such as its perfuming effect. Because some of the volatile $C_{6-20}$ perfuming aldehydes and $C_{6-20}$ perfuming ketones described above can also have insect attractant or repellent, pharmaceutical, bactericide, fungicide or malodor counteracting properties, it is evident that the invention's polymer microparticles, or latexes, can also be used in formulations serving for insect attractant or repellent, pharmaceutical, bactericide, fungicide or malodor counteracting purposes. Indeed, said polymer microparticles, or latexes, possess several other properties that make it particularly suitable for this purpose.

The proportions in which the polymer microparticle according to the invention can be incorporated into the various aforementioned articles or compositions vary within a wide range of values. These values are dependent upon the nature of the article or product to be perfumed and on the desired olfactory effect as well as the nature of the co-ingredients in a given composition when the compounds according to the invention are mixed with perfuming co-ingredients, solvents or additives commonly used in the art.

For example, typical concentrations are in the order of 0.001% to 20% by weight, or even more, of the invention's polymer microparticle or latex based on the weight of the composition into which they are incorporated. Concentrations lower than these, such as in the order of 0.001% to 5% by weight, can be used when this polymer microparticle is applied directly in the perfuming of the various consumer products mentioned hereinabove.

Another object of the present invention relates to a method for the perfuming of a surface or to a method for intensifying or prolonging the diffusion effect of the characteristic fragrance of an odoriferous ingredient on a surface, characterized in that said surface is treated in the presence of an invention's polymer microparticle or latex. Suitable surfaces are, in particular, textiles, hard surfaces, hair and skin.

BRIEF DESCRIPTION OF THE DRAWINGS

FIG. 1: Dynamic headspace analysis for the evaporation of pure 2-phenylacetaldehyde, or of 2-phenylacetaldehyde released from 2-phenylethyl 2-oxo-2-phenylacetate or from Latex 1a in a fabric softener application (FIG. 1a: under xenon lamp; FIG. 1b: under daylight).

FIG. 2: Dynamic headspace analysis for the evaporation of pure citral or of citral released from Latex 2 in a fabric softener application.

FIG. 3: Dynamic headspace analysis for the evaporation of (Z)-3-hexenal or of (Z)-3-hexenal from Latex 3 in a fabric softener application.

FIG. 4: Olfactive panel evaluation of the intensity of the light-induced release of 2-phenylacetaldehyde from 2-phenylethyl 2-oxo-2-phenylacetate and from Latices 1a and 1b in a freshly prepared day cream.

FIG. 5: Olfactive panel evaluation of the intensity of the light-induced release of 1-decenal from Latex 5a in a freshly prepared day cream. (FIG. 5a: under xenon lamp; FIG. 5b: under daylight).

FIG. 6: Olfactive panel evaluation of the intensity of the light-induced release of 2-phenylacetaldehyde from 2-phenylethyl 2-oxo-2-phenylacetate and from Latices 1a and 1c in a day cream after storage for 3 months at 45° C.

FIG. 7: Dynamic headspace analysis for the evaporation of pure 2-phenylacetaldehyde or of 2-phenylacetaldehyde (FIG. 7a) or decanal (FIG. 7b) released from Latices 1a and 5b, respectively, in an all purpose surface cleaner application.

FIG. 8: Decomposition reaction of an invention's polymer wherein it is released citronellal.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) on a Bruker DPX 400 spectrometer with 400 MHz for $^1H$ and 100.6 MHz for $^{13}C$, the chemical displacements δ are indicated in ppm with respect to $Si(CH_3)_4$ (TMS) as standard, br. represents a broad signal. Dynamic Light Scattering (DLS) measurements were performed with a Zetasizer, Nanoseries, Nano-ZS apparatus (Malvern Instruments, UK) equipped with a 4 mW He—Ne laser at a wavelength of 633 nm. Scattered intensities were measured at 90° and 20° C.

Some of the polymers in the following examples comprise units with a pyrene moiety, this moiety is present to allow an analysis by fluorescence.

Example 1

Preparation of a Latex Based on 2-phenylethyl 2-oxo2-(4-vinylphenyl)acetate (Latex 1, Which is Capable of Releasing 2-phenylacetaldehyde)

(a) Synthesis of bis(2-phenylethyl)oxalate

Oxalyl chloride (10.2 g, 80.4 mmol) was added dropwise during 20 min to a stirred solution of 2-phenylethanol (20.0 g, 163.7 mmol) in pyridine (165 mL) at 0° C. The reaction mixture was allowed to warm to room temperature overnight. Ether was added (300 mL, 2×) and the mixture extracted with $H_2SO_4$ (10%, 300 mL, 3×), a saturated solution of $NaHCO_3$ (300 mL, 3×) and a saturated solution of NaCl (300 mL, 2×, pH 6). The organic layer was dried ($Na_2SO_4$) and concentrated. Column chromatography ($SiO_2$, heptane/diethyl ether 1:1) gave 20.1 g (84%) of a solid.

$^1$H-NMR ($CDCl_3$): 7.26 (m, 10H), 4.46 (t, 4H), 3.03 (m, 4H).

$^{13}$C-NMR (CDCl$_3$): 157.47, 136.67, 128.93, 128.62, 126.86, 67.35, 34.62.

(b) Synthesis of 2-phenylethyl 2-oxo-2-(4-vinylphenyl)acetate

A Grignard reagent prepared from freshly distilled 4-bromostyrene (9.45 g, 51.6 mmol) and magnesium (1.31 g, 54.0 mmol) in THF (70 mL) was added dropwise to a stirred solution of bis(2-phenylethyl)oxalate (14.0 g, 46.9 mmol) in THF (120 mL) at −60° C. The mixture was left warming to room temperature, and then poured onto a mixture of ice (200 g) and a saturated solution of NH$_4$Cl (200 mL). Extraction with diethyl ether (500 mL), washing with a saturated solution of NaCl (300 mL, 3×), re-extraction of the aqueous phase with ether, drying of the combined organic phases (Na$_2$SO$_4$), adding of tert-butyl hydroquinone (TBHQ, ca. 0.3 mg), concentrating and drying under vacuum (0.5 mbar, 0.5 h) afforded 19.40 g of the crude compound. Column chromatography (SiO$_2$, heptane/ethyl acetate 98:2), adding of TBHQ (0.2 mg) to the product fractions, concentrating and drying under vacuum gave 8.95 g (68%) of the desired compound.

$^1$H-NMR (CDCl$_3$): 7.82 (d, 2H), 7.45 (d, 2H), 7.28 (m, 5H), 6.74 (dd, 1H), 5.90 (d, 1H), 5.45 (d, 1H), 4.61 (t, 2H), 3.08 (t, 2H).

$^{13}$C-NMR (CDCl$_3$): 185.59, 163.71, 143.83, 136.98, 135.71, 131.49, 130.47, 129.01, 128.69, 126.85, 126.53, 117.97, 66.39, 34.95.

(c) Preparation of a Cross-linked Random Co-polymer of Methyl Methacrylate, 2-phenylethyl 2-oxo-2-(4-vinylphenyl)acetate and 1,4-butanediol divinyl ether (Diameter=356 nm, Latex 1a)

Methyl methacrylate (0.60 g, 6.01 mmol), 2-phenylethyl 2-oxo-2-(4-vinylphenyl)acetate (1.12 g, 4.00 mmol), 1,4-bis(vinyloxy)butane (1.70 mg, 12.0 µmol) and poly(ethylene glycol)-block-poly(propylene glycol)-block-poly(ethylene glycol) (0.17 g) were mixed in water (6.65 mL) to give a yellow emulsion. The reaction mixture was stirred at 24000 rpm with an ultra-turrax at room temperature for 2 min and then transferred to a 25 mL round-bottomed flask and stirred at 400 rpm. A solution of 2,2'-azobis(2-methylpropionamidine)dihydrochloride (35.90 mg, 6.01 µmol) in water (0.50 mL) was added and the reaction mixture was stirred at 70° C. for 4 h. Additional 2,2'-azobis(2-methylpropionamidine)dihydrochloride (21.00 mg, 4.61 µmol) was added. The reaction mixture was stirred at 70° C. for 2 h 30. The medium was slowly cooled to room temperature under stirring. Thermogravimetric analysis (TGA) indicated a solid content of 21.6% and DLS a diameter of 356 nm.

$^1$H-NMR (CDCl$_3$): 7.73 (m, 2H), 7.26 (m, 5H), 7.09 (m, 2H), 4.59 (m, 2H), 3.59 (m, 6H), 3.08 (m, 2H), 1.80 (m, 8H), 0.83 (m, 8H).

$^{13}$C-NMR (CDCl$_3$): 185.64, 178.08, 177.82, 176.89, 163.59, 136.91, 130.29, 129.95, 129.01, 128.69, 126.89, 51.80, 51.04, 45.66, 44.80, 44.51, 34.94, 18.73, 16.51.

(d) Preparation of a Cross-linked Random Co-polymer of Methyl Methacrylate, 2-phenylethyl 2-oxo-2-(4-vinylphenyl)acetate and 1,4-butanediol divinyl ether (Diameter=1.28 µm, Latex 1b)

Methyl methacrylate (0.461 g, 4.61 mmol), 2-phenylethyl 2-oxo-2-(4-vinylphenyl)acetate (0.53 g, 1.90 mmol), 1,4-bis(vinyloxy)butane (1.00 mg, 7.03 µmol) and poly(ethylene glycol)-block-poly(propylene glycol)-block-poly(ethylene glycol) (0.10 g) were mixed in water (3.30 mL) to give a yellow suspension. The reaction mixture was stirred at 24000 rpm with an ultra-turrax at room temperature for 2 min and then transferred to a 25 mL round-bottomed flask and stirred at 400 rpm. A solution of 2,2'-azobis(2-methylpropionamidine)dihydrochloride (19.80 mg, 4.61 µmol) in water (0.50 mL) was added and the reaction mixture was stirred at 70° C. for 4 h. Additional 2,2'-azobis(2-methylpropionamidine)dihydrochloride (21.00 mg, 4.61 mmol) was added. The reaction mixture was stirred at 70° C. for 2 h. The medium was slowly cooled to room temperature under stirring. TGA indicated a solid content of 29.9% and DLS a diameter of 1.28 µm.

(e) Preparation of a Cross-linked Random Co-polymer of Methyl Methacrylate, N-(pyren-1-ylmethyl)methacrylamide, 2-phenylethyl 2-oxo-2-(4-vinylphenyl)acetate and 1,4-butanediol divinyl ether (Latex 1c)

Methyl methacrylate (0.61 g, 6.01 mmol), 2-phenylethyl 2-oxo-2-(4-vinylphenyl)acetate (1.12 g, 4.00 mmol), N-(pyren-1-ylmethyl)methacrylamide (1.50 mg, 5.01 µmol), 1,4-bis(vinyloxy)butane (1.70 mg, 12.0 µmol) and poly(ethylene glycol)-block-poly(propylene glycol)-block-poly(ethylene glycol) (0.17 g) were mixed in water (6 mL) to give a yellow suspension. The reaction mixture was stirred at 24000 rpm with an ultra-turrax at room temperature for 2 min and then transferred to a 25 mL round-bottomed flask and stirred at 400 rpm. A solution of 2,2'-azobis(2-methylpropionamidine)dihydrochloride (34.70 mg) in water (0.50 mL) was added and the reaction mixture was stirred at 70° C. for 4 h. Additional 2,2'-azobis(2-methylpropionamidine)dihydrochloride (3.70 mg) was added and the reaction mixture was stirred at 70° C. for 2.5 h. The reaction mixture was cooled to room temperature under stirring. TGA indicated a solid content of 17.8% and DLS a diameter of 349 nm.

(f) Preparation of a Cross-linked Random Co-polymer of n-butyl methacrylate, N-(pyren-1-ylmethyl)methacrylamide, 2-phenylethyl 2-oxo-2-(4-vinylphenyl)acetate and 1,4-butanediol divinyl ether (Latex 1d)

In a 10 mL beaker, a solution of 2-phenylethyl 2-oxo-2-(4-vinylphenyl)acetate (1.14 g, 4.05 mmol), n-butyl methacrylate (0.86 g, 6.06 mmol), 1,4-bis(vinyloxy)butane (3.20 mg, 0.02 mmol) and N-(pyren-1-ylmethyl)methacrylamide (2.00 mg, 6.68 µmol) was added to a solution of poly(vinyl pyrrolidone) PVP K30 (origin: Aldrich, 0.40 g) in water (16 mL) to give a yellow suspension. An emulsion was obtained with an ultra-turrax (24000 rpm for 2 min). The reaction mixture was transferred to a 25 mL round-bottomed flask and stirred at 400 rpm. A solution of 2,2'-azobis(2-methylpropionamidine)dihydrochloride (35 mg, 4.05 mmol) in water (0.5 mL) was added. The reaction mixture was stirred at 70° C. for 2 h. A second solution of 2,2'-azobis(2-methylpropionamidine)dihydrochloride (34 mg, 4.05 mmol) in water (0.5 mL) was added and the reaction mixture was stirred at 70° C. for a total time of 24 h. The suspension was slowly cooled to room temperature under stirring.

(g) Preparation of a Cross-linked Random Co-polymer of Vinyl Acetate, N-(pyren-1-ylmethyl)methacrylamide, 2-phenylethyl 2-oxo-2-(4-vinylphenyl)acetate and 1,4-butanediol divinyl ether (Latex 1e)

In a 10 mL beaker, a solution of 2-phenylethyl 2-oxo-2-(4-vinylphenyl)acetate (1.12 g, 4.01 mmol), vinyl acetate (0.35 g, 4.04 mmol), 1,4-bis(vinyloxy)butane (3.20 mg, 0.02 mmol) and N-(pyren-1-ylmethyl)methacrylamide (1.50 mg, 5.01 µmol) was added to a solution of PVP K30 (0.44 g) in water (12 mL) to give a yellow suspension. An emulsion was obtained with an ultra-turrax (24000 rpm for 2 min). The reaction mixture was transferred to a 25 mL round-bottomed flask and stirred at 400 rpm. A solution of 2,2'-azobis(2-methylpropionamidine)dihydrochloride (36.80 mg) in water (0.5 mL) was added. The reaction mixture was stirred at 70° C. for 2 h. A second solution of 2,2'-azobis(2-methylpropionamidine)dihydrochloride (36.7 mg) in water (0.5 mL) was added and the reaction mixture was stirred at 70° C. for a total time of 48 h. The suspension was slowly cooled to room temperature under stirring.

(h) Preparation of a Cross-linked Random Co-polymer of Styrene, N-(pyren-1-ylmethyl)methacrylamide, 2-phenylethyl 2-oxo-2-(4-vinylphenyl)acetate and 1,4-butanediol Divinyl Ether by Dispersion Polymerization in Ethanol (Latex 1f).

In a 50 mL beaker, 2-phenylethyl 2-oxo-2-(4-vinylphenyl) acetate (1.95 g, 6.96 mmol), 1,4-bis(vinyloxy)butane (0.31 g, 0.02 mmol), N-(pyren-1-ylmethyl)methacrylamide (3.08 mg, 10.30 µmol), and styrene (1.08 g, 10.32 mmol) were added to a solution of PVP K30 (0.36 g) in ethanol (5.60 g) to give a solution. The reaction mixture was transferred to a 25 mL round-bottomed flask and stirred at 200 rpm. A solution of 2,2'-azobis(2-methylpropionitrile) (AIBN, 0.11 g, 0.66 mmol) in ethanol (5 g) was added and the reaction mixture was stirred at 70° C. for 15 h. The medium was finally cooled to room temperature under stirring to give a dispersion.

(i) Preparation of a Random Co-polymer of 2-[2-(2-methoxyethoxy)ethoxy]ethyl 4-vinylbenzoate and 2-phenylethyl 2-oxo-2-(4-vinylphenyl)acetate (Latex 1g)

2-[2-(2-methoxyethoxy)ethoxy]ethyl 4-vinylbenzoate (1.58 g, 5.36 mmol) and 2-phenylethyl 2-oxo-2-(4-vinylphenyl)acetate (0.5 g, 1.79 mmol) were added to a solution of AIBN (90 mg) in dry THF (30 mL, distilled over KNa). The reaction mixture was stirred at 80° C. for 19 h. More AIBN (90 mg) was added and the reaction heated for another 24 h. After cooling to room temperature, methanol (50 mL) was added, then the product was concentrated and taken up in THF (3 mL). This procedure was repeated 3 times. The solvent was evaporated and the product taken up in THF (3 mL). Heptane was added (3 mL) and, after stirring for a couple of minutes, the supernatant solution was pipetted off and the product concentrated. This procedure was repeated 8 times. Concentrating and drying under vacuum (ca. 0.2 mbar, 2 h) finally gave 1.46 g of a yellow oil.

Example 2

Preparation of a Latex Based on (E)-3,7-dimethylocta-2,6-dien-1-yl 2-oxo-2-(4-vinylphenyl)acetate (Latex 2, which is Capable of Releasing Citral)

(a) Synthesis of (E)-bis(3,7-dimethylocta-2,6-dien-1-yl)oxalate

Oxalyl chloride (12.5 g, 98.5 mmol) was added dropwise during 20 min to a stirred solution of (E)-3,7-dimethylocta-2,6-dien-1-ol (geraniol, 30.4 g, 197.1 mmol) in pyridine (200 mL) at 0° C. The reaction mixture was allowed to warm up to room temperature during the week-end and hydrolysed with water (100 mL, exothermic reaction). Ether was added (200 mL, 2×) and the mixture extracted with $H_2SO_4$ (10%, 100 mL, 3×), a saturated solution of $NaHCO_3$ (100 mL, 3×) and a saturated solution of NaCl (100 mL). The organic layer was dried ($Na_2SO_4$) and concentrated. Column chromatography ($SiO_2$, heptane/diethyl ether 4:1) and bulb-to-bulb distillation (70° C., 0.1 mbar) gave 26.3 g (74%) of an oil.

$^1$H-NMR (CDCl$_3$): 5.41 (t, 2H), 5.07 (t, 2H), 4.80 (d, 4H), 2.08 (m, 8H), 1.74 (s, 6H), 1.67 (s, 6H), 1.59 (s, 6H).

$^{13}$C-NMR (CDCl$_3$): 157.97, 144.27, 131.98, 123.57, 116.83, 63.81, 39.55, 26.19, 25.66, 17.69, 16.58.

(b) Synthesis of (E)-3,7-dimethylocta-2,6-dien-1-yl 2-oxo-2-(4-vinylphenyl)acetate A Grignard reagent prepared from 4-bromostyrene (2.78 g, 15.2 mmol) and magnesium (0.39 g, 15.9 mmol) in THF (23 mL) was added dropwise (during 20 min) to a stirred solution of (E)-bis(3,7-dimethylocta-2,6-dien-1-yl)oxalate (5.00 g, 13.8 mmol) in THF (40 mL) at −60° C. The mixture was left warming to room temperature, and then poured into a mixture of ice (70 g) and a saturated solution of $NH_4Cl$ (60 mL). Extraction with diethyl ether (200 mL), washing with a saturated solution of NaCl (100 mL, 3×), drying ($Na_2SO_4$), adding of hydroquinone (10 mg) and concentrating afforded 6.44 g of the crude compound. Repetitive column chromatography ($SiO_2$, heptane/ether 9:1 and 98:2), addition of hydroquinone to the product fraction, concentration and drying under vacuum (0.2 mbar, 1 h) gave 0.90 g (21%) of an oil.

$^1$H-NMR (CDCl$_3$): 7.97 (d, 2H), 7.51 (d, 2H), 6.76 (dd, 1H), 5.92 (d, 1H), 5.45 (m, 2H), 5.09 (m, 1H), 4.90 (d, 2H), 2.10 (m, 4H), 1.77 (s, 3H), 1.67 (s, 3H), 1.60 (s, 3H).

$^{13}$C-NMR (CDCl$_3$): 185.79, 163.90, 144.38, 143.82, 135.74, 132.03, 131.71, 130.49, 126.57, 123.56, 117.94, 117.09, 116.80, 62.99, 39.56, 26.25, 25.68, 17.71, 16.63.

(c) Preparation of a Cross-linked Random Co-polymer of Methyl Methacrylate, (E)-3,7-dimethylocta-2,6-dien-1-yl 2-oxo-2-(4-vinylphenyl)acetate, and 1,4-butanediol divinyl ether (Latex 2)

Methyl methacrylate (0.50 g, 5.02 mmol), (E)-3,7-dimethylocta-2,6-dien-1-yl 2-oxo-2-(4-vinylphenyl)acetate (1.03 g, 3.30 mmol), 1,4-bis(vinyloxy)butane (1.50 mg, 10.55 µmol) were mixed. Poly(ethylene glycol)-block-poly (propylene glycol)-block-poly(ethylene glycol) (0.15 g) and water (5.97 mL) were added. The reaction mixture was stirred at 24000 rpm with an ultra-turrax at room temperature for 5 min and then transferred to a 25 mL round-bottomed flask and stirred at 400 rpm. 2,2'-Azobis(2-methylpropionamidine)dihydrochloride (30.90 mg, 5.02 mmol) was added and the reaction mixture was stirred at 70° C. for 4 h. Additional 2,2'-azobis(2-methylpropionamidine)dihydrochloride (33.40 mg, 5.02 mmol) was added. TGA indicated a solid content of 16.6%.

Example 3

Preparation of a Latex Based on (Z)-3-hexenyl 2-oxo-2-(4-vinylphenyl)acetate (Latex 3, which is Capable of Releasing (Z)-3-hexenal)

(a) Synthesis of bis[(Z)-3-hexenyl]oxalate

Oxalyl chloride (12.7 g, 100.0 mmol) was added dropwise during 20 min to a stirred solution of (Z)-3-hexenol (20.0 g, 200.0 mmol) in pyridine (240 mL) at 0° C. The reaction mixture was allowed to warm up to room temperature during the week-end, then added to $H_2SO_4$ (50%, containing ice, 400 mL), extracted with ether (400 mL and 200 mL), treated again with $H_2SO_4$ (50%, containing ice, 400 mL), washed with a saturated solution of NaCl (200 mL) and a saturated solution of $NaHCO_3$ (200 mL, 2×). The organic layer was dried ($Na_2SO_4$) and concentrated. Column chromatography ($SiO_2$, heptane/diethyl ether 9:1) gave, after drying under vacuum (0.5 mbar, 1 h), 20.9 g (82%) of an oil.

$^1$H-NMR (CDCl$_3$): 5.54 (m, 2H), 5.32 (m, 2H), 4.27 (t, 4H), 2.48 (q, 4H), 2.07 (quint., 4H), 0.97 (t, 6H).

$^{13}$C-NMR (CDCl$_3$): 157.84, 135.41, 122.57, 66.35, 26.42, 20.62, 14.16.

(b) Synthesis of (Z)-3-hexenyl 2-oxo-2-(4-vinylphenyl)acetate

A Grignard reagent prepared from 4-bromostyrene (6.95 g, 38.0 mmol) and magnesium (0.97 g, 39.9 mmol) in THF (100 mL) was added dropwise (during a period of 20 min) to a stirred solution of bis[(Z)-3-hexenyl]oxalate (9.20 g, 36.2 mmol) in THF (35 mL) at −60° C. The mixture was left warming to room temperature and poured into a mixture of ice (100 g) and a saturated solution of NH$_4$Cl (100 mL). Extraction with diethyl ether (200 mL, 2×), washing with a saturated solution of NaCl (50 mL, 4×, pH 7), drying (Na$_2$SO$_4$) and concentrating afforded 11.47 g of the crude compound as a brownish oil. Bulb-to-bulb distillation of 8.68 g of the crude product (0.06 mbar, 60° C.) and column chromatography (SiO$_2$, heptane/ether 95:5, then 1:1, then pure ether) gave 3.53 g (50%) of an oil.

$^1$H-NMR (CDCl$_3$): 7.97 (d, 2H), 7.51 (d, 2H), 6.75 (dd, 1H), 5.92 (d, 1H), 5.54 (m, 1H), 5.44 (d, 1H), 5.35 (m, 1H), 4.39 (t, 2H), 2.53 (q, 2H), 2.06 (quint., 2H), 0.94 (t, 3H).

$^{13}$C-NMR (CDCl$_3$): 185.67, 163.87, 143.87, 135.72, 135.35, 131.60, 130.49, 126.57, 122.88, 117.98, 65.60, 26.63, 20.65, 14.15.

(c) Preparation of a Cross-linked Random Co-polymer of Methyl Methacrylate, (Z)-3-hexenyl 2-oxo-2-(4-vinylphenyl)acetate and 1,4-butanediol divinyl ether (Latex 3)

Methyl methacrylate (0.56 g, 5.57 mmol), (Z)-3-hexenyl 2-oxo-2-(4-vinylphenyl)acetate (1.01 g, 3.90 mmol), and 1,4-bis(vinyloxy)butane (1.60 mg, 0.01 mmol) were mixed to give a yellow solution. Poly(ethylene glycol)-block-poly(propylene glycol)-block-poly(ethylene glycol) (0.16 g) and water (5.80 mL) were added. The reaction mixture was stirred at 24000 rpm with an ultra-turrax at room temperature for 5 min and then transferred to a 25 mL round-bottomed flask and stirred at 400 rpm. 2,2'-Azobis(2-methylpropionamidine)dihydrochloride (30.90 mg, 5.02 mmol) was added and the reaction mixture was stirred for 4 h at 70° C. TGA indicated a solid content of 21.9%.

$^1$H-NMR (CDCl$_3$): 7.86 (m, 2H), 7.02 (m, 2H), 5.55 (m, 1H), 5.35 (m, 2H), 4.38 (m, 2H), 3.59 (m, 3H), 2.54 (m, 2H), 2.07 (m, 2H), 0.96 (m, 7H).

$^{13}$C-NMR (CDCl$_3$): 185.72, 177.85, 176.93, 163.76, 135.42, 130.31, 128.44, 122.84, 70.58, 66.35, 65.61, 54.41, 51.80, 51.02, 45.57, 44.90, 44.53, 26.62, 26.40, 20.65, 18.74, 17.47, 16.50, 14.19.

Example 4

Preparation of a Latex Based on (1R,2S,5R)-2-isopropyl-5-methylcyclohexyl 2-oxo-2-(4-vinylphenyl)acetate (Latex 4, which is Capable of Releasing (−)-menthone)

(a) Synthesis of bis[(1R,2S,5R)-2-isopropyl-5-methylcyclohexyl]oxalate

Oxalyl chloride (12.1 g, 96.2 mmol) was added dropwise during 20 min to a stirred solution of (−)-menthol (30.0 g, 192.0 mmol) in pyridine (240 mL) at 0° C. The reaction mixture was allowed to warm up to room temperature overnight, then added to H$_2$SO$_4$ (50%, containing ice, 400 mL), extracted with ether (400 mL and 200 mL), treated again with H$_2$SO$_4$ (50%, containing ice, 400 mL), washed with a saturated solution of NaCl (200 mL) and a saturated solution of NaHCO$_3$ (200 mL, 2×). The organic layer was dried (Na$_2$SO$_4$) and concentrated. Column chromatography (SiO$_2$, heptane/diethyl ether 9:1) gave, after drying under vacuum (0.5 mbar, 1 h), 26.2 g (74%) of an oil.

$^1$H-NMR (CDCl$_3$): 4.82 (td, 2H), 2.07 (m, 2H), 1.88 (m, 2H), 1.70 (m, 4H), 1.11 (m, 4H), 0.91 (dd, 12H), 0.78 (d, 6H).

$^{13}$C-NMR (CDCl$_3$): 158.19, 77.55, 46.71, 40.27, 34.05, 31.43, 26.38, 23.64, 21.93, 20.55, 16.47.

(b) Synthesis of (1R,2S,5R)-2-isopropyl-5-methylcyclohexyl 2-oxo-2-(4-vinylphenyl)acetate A Grignard reagent prepared from 4-bromostyrene (2.75 g, 15.0 mmol) and magnesium (0.39 g, 16.0 mmol) in THF (20 mL) was added dropwise (during a period of 20 min) to a stirred solution of bis[(1R,2S,5R)-2-isopropyl-5-methylcyclohexyl]oxalate (5.00 g, 13.7 mmol) in THF (15 mL) at −60° C. The mixture was left warming to room temperature and poured into a mixture of ice (200 g) and a saturated solution of NH$_4$Cl (10 mL). Extraction with diethyl ether (2×), washing with water (3×), drying (Na$_2$SO$_4$) and concentrating afforded 6.42 g of the crude compound as an oil. Repetitive column chromatography (SiO$_2$, heptane/ether 7:3 and heptane/ether 95:5) gave 2.03 g (47%) of an oil.

$^1$H-NMR (CDCl$_3$): 7.94 (d, 2H), 7.52 (m, 2H), 6.76 (dd, 1H), 5.92 (d, 1H), 5.45 (d, 1H), 5.00 (td, 1H), 2.18 (m, 1H), 1.95 (m, 1H), 1.73 (m, 2H), 1.18 (m, 2H), 0.95 (d, 3H), 0.90 (d, 3H), 0.84 (d, 3H).

$^{13}$C-NMR (CDCl$_3$): 186.18, 163.91, 143.78, 135.75, 131.71, 130.35, 126.61, 117.91, 46.82, 40.64, 34.07, 31.56, 26.17, 23.34, 21.97, 20.69, 16.16.

(c) Preparation of a Cross-linked Random Co-polymer of Methyl Methacrylate, (1R,2S,5R)-2-isopropyl-5-methylcyclohexyl 2-oxo-2-(4-vinylphenyl)acetate and 1,4-butanediol divinyl ether (Latex 4a)

Methyl methacrylate (0.59 g, 5.90 mmol), (1R,2S,5R)-2-isopropyl-5-methylcyclohexyl 2-oxo-2-(4-vinylphenyl)acetate (1.22 g, 3.90 mmol), and 1,4-bis(vinyloxy)butane (1.80 mg, 0.01 mmol) were mixed to give a yellow solution. Poly(ethylene glycol)-block-poly(propylene glycol)-block-poly(ethylene glycol) (0.19 g) and water (5.80 mL) were added. The reaction mixture was stirred at 24000 rpm with an ultra-turrax at room temperature for 5 min and then transferred to a 25 mL round-bottomed flask and stirred at 400 rpm. 2,2'-Azobis(2-methylpropionamidine)dihydrochloride (18.00 mg, 5.02 mmol) was added and the reaction mixture was stirred for 4 h at 70° C. TGA indicated a solid content of 17.2%.

(d) Preparation of a Cross-linked Random Co-polymer Based on Methyl Methacrylate, (1R,2S,5R)-2-isopropyl-5-methylcyclohexyl 2-oxo-2-(4-vinylphenyl)acetate, N-(pyren-1-ylmethyl)methacrylamide, and 1,4-butanediol divinyl ether (Latex 4b)

Methyl methacrylate (0.60 g, 6.02 mmol), (1R,2S,5R)-2-isopropyl-5-methylcyclohexyl 2-oxo-2-(4-vinylphenyl)acetate (1.26 g, 3.98 mmol), N-(pyren-1-ylmethyl)methacrylamide (1.50 mg, 5.01 μmol), and 1,4-bis(vinyloxy)butane (1.60 mg, 0.01 mmol) were mixed to give a yellow solution. Poly(ethylene glycol)-block-poly(propylene glycol)-block-poly(ethylene glycol) (0.17 g) and water (10 mL) were added. The reaction mixture was stirred at 24000 rpm with an ultra-turrax at room temperature for 2 min and then transferred to a 25 mL round-bottomed flask and stirred at 400 rpm. A solution of 2,2'-azobis(2-methylpropionamidine)dihydrochloride (38.50 mg, 3.98 mmol) in water (0.50 mL) was added and the reaction mixture was stirred for 25 h at 70° C. A second solution of 2,2'-azobis(2-methylpropionamidine)dihydrochloride (37.50 mg, 3.96 mmol) in water (0.50 mL) was added and the reaction mixture was stirred for 2 h 30 at 70° C. The reaction mixture was slowly cooled down to room temperature to give a dispersion.

(e) Preparation of poly[(1R,2S,5R)-2-isopropyl-5-methylcyclohexyl 2-oxo-2-(4-vinylphenyl)acetate] (Latex 4c)

(1R,2S,5R)-2-isopropyl-5-methylcyclohexyl 2-oxo-2-(4-vinylphenyl)acetate (2.00 g, 6.37 mmol) was added to a solution of AIBN (80 mg) in dry THF (30 mL, distilled over KNa). The reaction mixture was stirred at 80° C. for 2 days. After cooling to room temperature, ethanol (50 mL) was added, then the product was concentrated and taken up in THF (5 mL). This procedure was repeated 8 times. The THF was evaporated and the product dried under vacuum (ca. 0.1 mbar, 2 h) to give 2.05 g of a yellow solid.

$^{13}$C-NMR (CDCl$_3$): 185.67 (br.), 163.55 (br.), 150.95 (br.), 131.24 (br.), 130.35 (br.), 130.17 (br.), 127.92 (br.), 77.24 (br.), 76.93 (br.), 46.78 (br.), 40.55 (br.), 34.07, 31.58, 26.17, 23.40, 22.00, 20.72, 16.24.

GPC (THF, polystyrene): M$_n$=6933 Da, M$_w$=17662 Da.

Example 5

Preparation of a Latex Based on decyl 2-oxo-2-(4-vinylphenyl)acetate (Latex 5, which is Capable of Releasing 1-decanal)

(a) Synthesis of didecyl oxalate

Oxalyl chloride (6.35 g, 50.0 mmol) was added dropwise during 25 min to a stirred solution of decanol (15.83 g, 100.0 mmol) in pyridine (7.91 g, 100 mmol) at 0° C. The reaction mixture was allowed to warm up to room temperature overnight. The reaction mixture was poured into a mixture of H$_2$SO$_4$ (50%, 400 mL) and ice (400 g) and extracted with ethyl acetate (200 mL). The aqueous phase was re-extracted with ethyl acetate. The combined organic phases were washed with H$_2$SO$_4$ (200 mL) and ice, a saturated solution of NaCl (100 mL) and a saturated solution of NaHCO$_3$ (100 mL, 2×). The organic layer was dried (Na$_2$SO$_4$) and concentrated. Column chromatography (SiO$_2$, heptane/ethyl acetate 7:3) gave 18.45 g (quant.) of an oil.

$^1$H-NMR (CDCl$_3$): 4.28 (t, 4H), 1.73 (quint., 4H), 1.43-1.20 (m, 28H), 0.88 (t, 6 H).

$^{13}$C-NMR (CDCl$_3$): 158.11, 67.17, 31.91, 29.53, 29.49, 29.32, 29.18, 28.31, 25.73, 22.70, 14.11.

(b) Synthesis of decyl 2-oxo-2-(4-vinylphenyl)acetate

A Grignard reagent prepared from 4-bromostyrene (5.86 g, 32.0 mmol) and magnesium in THF (45 mL) was added dropwise to a stirred solution of didecyl oxalate (10.82 g, 29.2 mmol) in THF (50 mL) at −70° C. The mixture was left warming to room temperature and poured onto a mixture of ice and a solution of NH$_4$Cl (10%, 50 mL). Extraction with ethyl acetate (100 mL, 2×), washing with water (100 mL, 2×), drying (Na$_2$SO$_4$) and concentrating afforded 12.00 g of the crude compound as an oil. Repetitive column chromatography (SiO$_2$, heptane/ethyl acetate 95:5 to 7:3) finally gave 3.98 g (43%) of an oil.

$^1$H-NMR (CDCl$_3$): 8.00-7.95 (m, 2H), 7.55-7.50 (m, 2H), 6.76 (dd, 1H); 5.92 (d, 1H), 5.46 (d, 1H), 4.38 (t, 2H), 1.82-1.73 (m, 2H), 1.46-1.21 (m, 14H), 0.88 (t, 3H).

$^{13}$C-NMR (CDCl$_3$): 185.82, 164.01, 143.85, 135.74, 131.68, 130.46, 126.58, 117.94, 66.38, 31.89, 29.51, 29.48, 29.30, 29.17, 28.48, 25.80, 22.68, 14.11.

(c) Preparation of poly[decyl 2-oxo-2-(4-vinylphenyl)acetate] (Latex 5a)

In a 25 mL round bottomed three necked flask, PVP K30 (0.042 g, 0.764 μmol) was dissolved in ethanol (0.850 mL). Decyl 2-oxo-2-(4-vinylphenyl)acetate (0.111 g, 0.352 mmol) and AIBN (0.011 g, 0.069 mmol) were added to the reaction mixture to give a colorless solution which was stirred at 45° C. for 72 h. The reaction mixture was finally slowly cooled to room temperature to give a dispersion having a particle diameter in ethanol near 1.3 μm as observed by light microscopy.

(d) Preparation of a Cross-linked Random Co-polymer of Methyl Methacrylate, decyl 2-oxo-2-(4-vinylphenyl)acetate], N-(pyren-1-ylmethyl)methacrylamide and 1,4-butanediol divinyl ether (Latex 5b)

In a 10 mL beaker, methyl methacrylate (0.60 g, 6.01 mmol), decyl 2-oxo-2-(4-vinylphenyl)acetate (1.26 g, 3.98 mmol), 1,4-bis(vinyloxy)butane (1.60 mg, 11 μmol), N-(pyren-1-ylmethyl)methacrylamide (1.5 mg, 5.01 μmol) and poly(ethylene glycol)-block-poly(propylene glycol)-block-poly(ethylene glycol) (0.17 g) were mixed in water (10 mL) to give a yellow suspension. The reaction mixture was stirred at 24000 rpm with an ultra-turrax at room temperature for 2 min and then transferred to a 25 mL round-bottomed flask and stirred at 400 rpm. A solution of 2,2'-azobis(2-methylpropionamidine)dihydrochloride (38.50 mg) in water (0.50 mL) was added and the reaction mixture was stirred at 70° C. for 25 h. A second solution of 2,2'-azobis(2-methylpropionamidine)dihydrochloride (37.50 mg) in water (0.5 mL) was added and the reaction mixture was stirred at 70° C. for 2 h 30. The medium was finally cooled to room temperature under stirring.

(e) Preparation of a Cross-linked Random Co-polymer of Styrene, decyl 2-oxo-2-(4-vinylphenyl)acetate and 1,4-butanediol divinyl ether (Latex 5c)

In a 10 mL beaker, a solution of decyl 2-oxo-2-(4-vinylphenyl)acetate (1.27 g, 4.00 mmol), 1,4-bis(vinyloxy)butane (0.01 g, 0.04 mmol), N-(pyren-1-ylmethyl)methacrylamide (1.9 mg, 6.35 μmol), and styrene (0.64 g, 6.14 mmol) was dispersed in a solution of PVP K30 (0.38 g) in water (16 mL) to give a yellow suspension. An emulsion was obtained with an ultra-turrax (24000 rpm for 2 min). The reaction mixture was transferred to a 25 mL round-bottomed flask and stirred at 400 rpm. A solution of 2,2'-azobis(2-methylpropionamidine)dihydrochloride (0.04 g) in water (0.5 mL) was added and the reaction mixture was stirred at 70° C. for 2 h. A second solution of 2,2'-azobis(2-methylpropionamidine)dihydrochloride (34 mg) in water (0.5 mL) was added and the reaction mixture was stirred at 70° C. for a total time of 20 h. The medium was slowly cooled to room temperature under stirring.

Example 6

Dynamic Headspace Analysis of the Release of a Perfuming Ingredient from Freshly Prepared Samples of the Invention's Co-polymers Incorporated into a Consumer Product (Fabric Softener)

A fabric softener base with the following final composition has been prepared:

| | |
|---|---|
| Stepantex® VL90 A (origin: Stepan) | 16.5% by weight |
| Calcium chloride (10% aq. solution) | 0.6% by weight |
| Water | 82.9% by weight |

In a small vial, a freshly prepared dispersion of Latex 1a described in Example 1 (0.026 mmol with respect to the total amount of fragrance to be released) was added to the fabric softener (1.8 g). Two freshly prepared reference samples consisting of an equimolar amount of pure 2-phenylacetaldehyde (0.026 mmol) and of 2-phenylethyl 2-oxo-2-phenylacetate (WO 99/60990) (0.026 mmol) in the fabric softener (1.8 g) were prepared in two additional vials, respectively. After homogenization, the samples were dispersed in a beaker with 600 mL of demineralized cold tap water. One cotton sheet (ca. 12×12 cm) was added to each beaker and agitated manually for 3 min, left standing for 2 min, then wrung out by hand, and weighed to obtain a constant quantity of residual water. The three sheets (one with Latex 1a, one with the 2-oxo-2-phenylacetate and one with the corresponding fragrance to be released) were line-dried for 24 h in the dark. The cotton sheets were then analyzed. For the measurements, the sheets with the latex or the 2-oxo-2-phenylacetate were put into a headspace sampling cell (ca. 160 mL inner volume) and irradiated with a xenon lamp (Heraeus Suntest CPS at about 90000 lux), whereas the sheet with the free fragrance was put into the headspace sampling cell exposed to natural indoor daylight. The headspace sampling cells were thermostated at 25° C. and exposed to a constant air flow of ca. 200 mL/min. The air was filtered through active charcoal and aspirated through a saturated solution of NaCl (to ensure a constant humidity of the air of ca. 75%). The volatiles were immediately adsorbed on a clean Tenax® cartridge for 10 min, then for 5 min on a waste cartridge. Then, four times consecutively, the volatiles were adsorbed for 10 min on a clean cartridge and 20 min on a waste cartridge. The waste cartridges were discarded; the other cartridges were desorbed on a Perkin Elmer TurboMatrix ATD 350 desorber coupled to a Perkin Elmer Autosystem XL gas chromatograph equipped with a J&W Scientific DB1 capillary column (30 m, i.d. 0.32 mm, film 1.50 μm) and a Perkin Elmer Turbomass Upgrade mass spectrometer. The volatiles were analyzed using a temperature gradient starting at 60° C. for 5 min, then going to 260° C. at 45° C./min. Headspace concentrations (in ng/L air) were obtained by external standard calibrations using five different 2-phenylacetaldehyde concentrations in methanol. Each calibration solution was injected onto a clean Tenax® cartridge, which was desorbed and analysed under the same conditions. The results obtained for the release of 2-phenylacetaldehyde are summarized in FIG. 1a.

As can be seen from FIG. 1a, the invention's latex performs better than the known prior art system by several times, even when freshly prepared samples were used (to avoid the stability problems of the prior art compound).

Similarly, another sample of Latex 1a was dispersed in the fabric softener and applied to a cotton sheet as described above. After 24 h of line drying, the cotton sheet was put into the headspace sampling cell and exposed to natural indoor daylight (ca. 9000 lux corresponding to plain sunlight behind the window). As the reference, samples of 2-phenylacetaldehyde and of 2-phenylethyl 2-oxo-2-phenylacetate (WO 99/60990) were prepared and analyzed under the same conditions. After equilibrating for 15 min, the volatiles were adsorbed on a clean Tenax® cartridge for 15 min, then for 45 min on a waste cartridge. The headspace sampling was repeated three times every hour. The waste cartridges were discarded; the other cartridges were desorbed as described above. The headspace data obtained are summarized in FIG. 1b (average values of two measurements).

The data obtained in FIG. 1b were different from those obtained by photoirradiation with xenon light, which is probably due to the lower light intensity. After 3 h of irradiation, the headspace concentration measured for Latex 1a was considerably higher than that recorded for 2-phenylethyl 2-oxo-2-phenylacetate and the unmodified raw material.

Example 7

Dynamic Headspace Analysis of the Release of a Perfuming Ingredient from Freshly Prepared Samples of the Invention's Co-polymers Incorporated into a Consumer Product (Fabric Softener)

As described in Example 6, dynamic headspace analysis was carried out to measure the release of 3,7-dimethylocta-2,6-dien-1-al (citral, 0.026 mmol with respect to the total amount of fragrance to be released) from Latex 2 described in Example 2. The release from this co-polymer was compared with a reference sample consisting of an equimolar amount of pure citral (0.026 mmol) in the fabric softener (1.8 g). The results are summarized in FIG. 2.

Similarly, dynamic headspace analysis was carried out to measure the release of (Z)-3-hexenal (0.026 mmol with respect to the total amount of fragrance to be released) from Latex 3 described in Example 3. The release from this co-polymer was compared with a reference sample consisting of an equimolar amount of pure (Z)-3-hexenal (0.026 mmol) in the fabric softener (1.8 g). The results are summarized in FIG. 3.

Example 8

Olfactive Evaluation of the Release of 2-phenylacetaldehyde from Fresh Samples of Latices 1a and 1b Incorporated into a Consumer Product (Day Cream)

The tests were carried out using a standard day cream formulated from Phases A-D and having the following final composition:

| | | |
|---|---|---|
| A | Arlacel® 985 (origin: Atlas Powder Company) | 5.0% by weight |
| | Cetyl alcohol (origin: Sigma-Aldrich) | 0.5% by weight |
| | Tefose® 2561 (origin: Gattefossé SA) | 4.0% by weight |
| | Biolip P 90 (Squalan) (origin: Gattefossé SA) | 1.0% by weight |
| | Mineral oil 30-40 CPS (Paraffin oil) | 2.0% by weight |
| | Petroleum jelly (Petrolatum) (origin: Holler & Co. GmbH) | 5.5% by weight |
| B | Water (deionized) | 76.2% by weight |
| | Propylene glycol | 5.0% by weight |
| C | Nipaguard PO 5 (phenoxyethanol (and) piroctone olamine) (origin: Clariant) | 0.6% by weight |
| D | PNC 400 (sodium carbomer) (origin: 3V International) | 0.2% by weight |

Phases A and B were heated separately to 70-75° C., then phase A was added to phase B. Vacuum was applied and the phases were mixed before the mixture was cooled to room temperature. The colloidal mill (Type MZ, incorporated in a Fryma VME-120 mixer and composed of a crosswise-toothed grinding set) was switched on (0.4 opening) during cooling from 65° C. to 55° C. (for ca. 15 min) Phase C (Nipaguard PO 5) was added at 45-50° C. and the mixture was kept mixing for 5 min before Phase D (PNC 400) was added. After 3 min, the colloidal mill was switched on (0.4 opening) and kept running for 15 min. The mixing was resumed at room temperature, at 30° C. the mill was switched on again for another 15 min until the cream became homogeneous, glossy and without lumps. Finally, if necessary, the pH was adjusted to the requested value (e.g. with a solution of citric acid).

Freshly prepared dispersions of Latices 1a and 1b obtained as described in Example 1 (0.05 wt % or 0.42 mM with respect to the total amount of fragrance to be released) were added to the above described day cream (20.0 g). Additionally, a reference sample consisting of 2-phenylethyl 2-oxo-2-phenylacetate (WO 99/60990, 0.42 mM) in the day cream (2.0 g) was prepared.

Aliquots of the day cream samples (0.15 g) containing the latices or 2-phenylethyl 2-oxo-2-phenylacetate, respectively, were then deposited onto a blotter and left for 1 h in the dark (at room temperature), or, alternatively, were exposed to light at 365 nm for 1 h at 22° C. (using an UVP Upland UVL-28 lamp, 365 nm, 8 W). The release of 2-phenylacetaldehyde from Latices 1a and 1b was assessed by sensory analysis (olfactive intensity) by 13 or 14 panelists. The panelists were asked to evaluate the intensity of the sample on a scale ranging from 0 (no odor) to 10 (very strong odor). The results obtained for the release of 2-phenylacetaldehyde are summarized in FIG. 4.

Example 9

Olfactive Evaluation of the Release of 1-decanal from Fresh Samples of Latex 5a Incorporated into a Consumer Product (Day Cream)

A day cream with the final composition as described in Example 8 has been prepared. Freshly prepared dispersions of Latex 5a obtained as described in Example 5 (0.05 wt % or 0.42 mM with respect to the total amount of fragrance to be released) were added to the above described day cream (20.0 g).

Aliquots of the day cream samples (0.15 g) containing Latex 5a were then deposited onto a blotter and left for 1 h in the dark (at room temperature), or, alternatively, were exposed to light at 365 nm for 1 h at 22° C. (using an UVP Upland UVL-28 lamp, 365 nm, 8 W). The release of 1-decanal from Latex 5a was assessed by sensory analysis (olfactive intensity) by 6 panelists. The panelists were asked to evaluate the intensity of the sample on a scale ranging from 0 (no odor) to 10 (very strong odor). The results obtained for the release of 1-decanal are summarized in FIG. 5a.

Similarly, another sample of Latex 5a in a day cream prepared as described above was exposed to natural indoor daylight for 3.25 h (plain sunlight behind the window). The release of 1-decanal from Latex 5a was assessed by sensory analysis (olfactive intensity) by 5 panelists as described above. The results obtained for the release of 1-decanal are summarized in FIG. 5b.

The data showed that the system successfully released the fragrance aldehyde upon exposure to artificial or natural light.

Example 10

Olfactive Evaluation of the Release of a Perfuming Ingredient from Aged Samples of Latices 1a and 1c Incorporated into a Consumer Product (Day Cream)

A day cream with the final composition as described in Example 8 has been prepared. A freshly prepared dispersion of Latices 1a and 1c obtained as described in Example 1 (0.05 wt % or 0.42 mM with respect to the total amount of fragrance to be released) was added to the above described day cream (20.0 g). Additionally, a reference sample consisting of 2-phenylethyl 2-oxo-2-phenylacetate (WO 99/60990, 0.42 mM) was prepared in the day cream (2.0 g). The samples were stored at 45° C. for 3 months. Aliquots of the day cream samples (0.15 g) containing Latices 1a or 1c, or 2-phenylethyl 2-oxo-2-phenylacetate, respectively, were then deposited onto a blotter and left for 1 h in the dark (at room temperature), or, alternatively, exposed to light at 365 nm for 1 h at 22° C. (using an UVP Upland UVL-28 lamp, 365 nm, 8 W). The release of 2-phenylacetaldehyde was assessed by sensory analysis (olfactive intensity) by 5 or 15 panelists. The panelists were asked to evaluate the intensity of the sample on a scale ranging from 0 (no odor) to 10 (very strong odor). The results obtained for the release of 2-phenylacetaldehyde are summarized in FIG. 6.

Only the sample containing Latices 1a and 1c gave a strong olfactive intensity of 2-phenylacetaldehyde after being exposed to light for 1 h.

Example 11

Stability of the Invention's Co-polymers in a Day Cream Measured by Dynamic Headspace Analysis A freshly prepared dispersion of Latex 1a obtained as described in Example 1 (0.05 wt % or 0.42 mM with respect to the total amount of fragrance to be released) was added to the day cream (20.0 g) described in the previous example. The release from this co-polymer was compared with a reference sample consisting of an equimolar amount of 2-phenylethyl 2-oxo-2-phenylacetate (WO 99/60990, 0.42 mM) in the day cream (2.0 g). The samples were stored at 3° C. and 45° C. for 3 months. Then each sample (2.15 g) was deposited onto two glass plates; one of the plates was stored in the dark for 1 h; the second was exposed to light at 365 nm for 1 h (using an UVP Upland UVL-28 lamp, to 365 nm, 8 W).

The different plates were put into two headspace sampling cells (28 mL inner volume) and a constant flow of nitrogen was passed over the samples (80 mL/min). At different time intervals, 1 mL of air above the different samples was taken with a gas-tight glass syringe and the concentration of 2-phenylacetaldehyde (from the desired light-induced fragmentation) and of 2-phenylethanol (from undesired premature solvolysis (hydrolysis) of the ester moiety) was measured by GC analysis for all samples. The data (expressed in wt %) are summarized in Tables 1 and 2. The 2-phenylacetaldehyde, used as the reference, was found to be unstable in the day cream at 3° C. with only 20% remaining after 3 months. The obtained headspace values based on this reference sample were corrected accordingly.

TABLE 1

Amounts of 2-phenylacetaldehyde and 2-phenylethanol released from a day cream sample containing 2-phenylethyl 2-oxo-2-phenylacetate or Latex 1a after storage at 3° C. for three months

| Day cream samples stored at 3° C. for 3 months containing | | | | |
|---|---|---|---|---|
| | 2-Phenylethyl 2-oxo-2-phenylacetate (WO 99/60990) | | Latex 1a | |
| Exposure | Dark | Light | Dark | Light |
| 2-Phenylacetaldehyde [wt %] | 0 | 2 | 0 | 16 |
| 2-Phenylethanol [wt %] | 50 | 52 | 1 | 0 |

The measurements showed that the samples containing the 2-phenylethyl 2-oxo-2-phenylacetate generated a significant amount of 2-phenylethanol (more than 50 wt %), due to premature hydrolysis of the profragrance. 2-Phenylacetaldehyde was not detected in the samples stored in the dark, and only 11% were detected after being exposed to light for 1 h. This result suggests that the majority of the 2-phenylethyl 2-oxo-2-phenylacetate described in the prior art hydrolyzes upon storage at 3° C.

On the other hand, the samples containing Latex 1a showed a modest release of 2-phenylethanol (1-2%) indicating a very low rate of hydrolysis. The corresponding aldehyde was not detected in the samples stored in the dark, whereas 16% of the desired aldehyde was released after exposure to light. This result suggests that the co-polymer according to the present invention efficiently prevents premature hydrolysis and allows the release of 2-phenylacetaldehyde upon exposure to light.

The same measurement was carried out with samples stored at 45° C. for 3 months. The results are summarized in Table 2.

TABLE 2

Amounts of 2-phenylacetaldehyde and 2-phenylethanol released from a day cream sample containing 2-phenylethyl 2-oxo-2-phenylacetate or Latex 1a after storage at 45° C. for three months
Day cream samples stored at 45° C. for 3 months containing

| Exposure | 2-Phenylethyl 2-oxo-2-phenylacetate (WO 99/60990) | | Latex 1a | |
|---|---|---|---|---|
| | Dark | Light | Dark | Light |
| 2-Phenylacetaldehyde [wt %] | 1 | 1 | 0 | 14 |
| 2-Phenylethanol [wt %] | 53 | 74 | 5 | 6 |

The measurements showed that the samples containing the 2-phenylethyl 2-oxo-2-phenylacetate generated a significant amount of 2-phenylethanol (more than 50 wt %), due to premature hydrolysis of the profragrance. About 5% of 2-phenylacetaldehyde were detected after being exposed to light for 1 h.

On the other hand, the samples containing Latex 1a showed the formation of only minor amounts of 2-phenylethanol, indicating a very low rate of hydrolysis in the samples stored in the dark, whereas 14% of the desired aldehyde was released after being exposed to light. This result suggests that the co-polymer according to the present invention is stable in a day cream after storage for 3 months at 45° C., but releases the desired aldehyde upon exposure to light.

Similarly, a day cream containing Latex 1c was prepared and analyzed as described above. The results are summarized in Tables 3 and 4. The samples containing Latex 1c showed the formation of more than 20% of the desired aldehyde after being exposed to light.

TABLE 3

Amounts of 2-phenylacetaldehyde released from a day cream sample containing Latex 1c after storage at 3° C. for three months
Day cream sample stored at 3° C. for 3 months containing

| Exposure | Latex 1c | | Ref 2-Phenylacetaldehyde |
|---|---|---|---|
| | Dark | Light | Light |
| 2-Phenylacetaldehyde [wt %] | 1 | 26 | 20 |

TABLE 4

Amounts of 2-phenylacetaldehyde released from a day cream sample containing Latex 1c after storage at 45° C. for three months
Day cream sample stored at 45° C. for 3 months containing

| Exposure | Latex 1c | | Ref 2-Phenylacetaldehyde |
|---|---|---|---|
| | Dark | Light | Light |
| 2-Phenylacetaldehyde [wt %] | 1 | 23 | 3 |

Example 12

Dynamic Headspace Analysis of the Release of a Perfuming Ingredient from Freshly Prepared Samples of the Invention's Co-polymers Incorporated into a Consumer Product (All Purpose Surface Cleaner)

The use as perfuming ingredient of the present invention's mixture has been tested in an all purpose cleaner (APC). An APC base with the following final composition has been prepared:

| Neodol® 91-8 (origin: Shell Chemicals) | 5.0% by weight |
| Marlon® A 375 (origin: Hüls AG) | 4.0% by weight |
| Sodium cumolsulphonate | 2.0% by weight |
| Kathon® CG (origin: Rohm and Haas) | 0.2% by weight |
| Water | 88.8% by weight |

The APC (1 mL) was added to a freshly prepared dispersion of Latex 1a described in Example 1 (0.012 mmol with respect to the total amount of fragrance to be released). The sample was then diluted by adding 9 mL of demineralized tap water. Another sample, serving as the reference, containing 2-phenylacetaldehyde (0.012 mmol) was prepared in the same way. The samples were then deposited as a film onto a porous ceramic plate (ca. 5×10 cm) by carefully pipetting 0.75 mL of the sample onto the surface of the substrate. The samples were then covered with a 2 L crystallizing dish and exposed to ambient indoor daylight at room temperature. After 24 h, the ceramic plate was placed inside a headspace sampling cell (ca. 625 mL). The sample with the latex was exposed to a xenon lamp (Heraeus Suntest CPS at about 90000 lux), while the reference sample with the free fragrance was exposed to indoor daylight. A constant air flow of ca. 200 mL/min was passed over the samples. The air was filtered through active charcoal and aspirated through a saturated solution of NaCl (to ensure a constant humidity of the air of ca. 75%). During 15 min the headspace system was left equilibrating, and then the volatiles were adsorbed on a clean Tenax® cartridge for 10 min, then for 20 min on a waste cartridge. Then, four times consecutively, the volatiles were adsorbed for 10 min on a clean cartridge and 20 min on a waste cartridge. The cartridges were desorbed on a Perkin Elmer TurboMatrix ATD desorber coupled to an Agilent 7890A gas chromatograph equipped with a HP 1 capillary column (30 m, i.d. 0.32 mm, film 0.25 μm) and a FID detector. The volatiles were analyzed by gas chromatography (GC) using a two step temperature gradient starting at 60° C., then going to 130° C. at 15° C./min, then to 220° C. at 40° C./min. Headspace concentrations (in ng/L air) were obtained by external standard calibrations using seven different 2-phenylacetaldehyde concentrations in ethanol. 0.2 μl of the different calibration solutions were injected onto Tenax® cartridges, which were immediately desorbed under the same conditions as those resulting from the headspace sampling. The measurements were carried out in duplicate. The results obtained for the release of 2-phenylacetaldehyde are summarized in FIG. 7a.

Similarly, an APC containing Latex 5b and another one containing an equimolar amount of decanal were prepared and analyzed as described above. The results are summarized in FIG. 7b.

As can be seen from FIG. 7, the invention's latices perform better than the free reference aldehydes by several orders of magnitude. After 25 min, almost 400 times more 2-phenylacetaldehyde was measured in the headspace above Latex 1a, and about 180 times more decanal was measured in the headspace above Latex 5b, as compared to the corresponding reference samples with the free aldehyde. After 145 min, still about 30 times more of both 2-phenylacetaldehyde and decanal were evaporated from the respective latices than from the reference.

What is claimed is:

1. A polymer microparticle capable of releasing in a controlled manner a perfuming aldehyde or ketone, said polymer microparticle comprising:
a) at least one repeating unit of formula

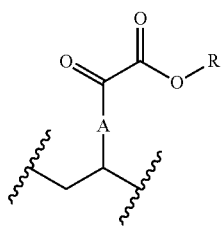

(I)

wherein A represents a benzene-1,4-diyl or a benzene-1,3-diyl moiety, and R is a group capable of releasing a $C_{6-20}$ perfuming aldehyde or perfuming ketone;
b) optionally at least one repeating cross-linking unit of formula

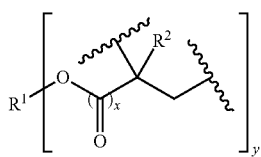

(II)

wherein all x are simultaneously either 0 or 1, y is 2, 3 or 4;
$R^1$ represents a $C_{2-12}$ hydrocarbon di-, tri- or tetra-radical depending upon the value of y, optionally comprising from 1 to 5 oxygen atoms; and
$R^2$ represents a hydrogen atom or a methyl group;
alternatively, the repeating cross-linking unit is of formula

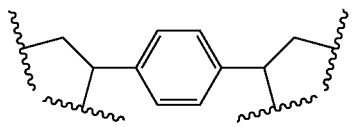

(III)

c) optionally at least one repeating unit of the formulae

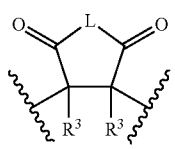

(IV-a)

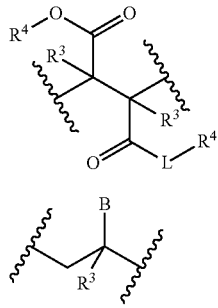

(IV-b)

(IV-c)

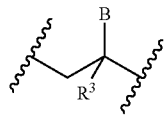

wherein L is an oxygen atom or a NH group, B represents a $COOR^4$ group, a $C_6H_5$, a $C_6H_4COOR^4$, a $OR^4$, a $R^4COO$, a $CON(R^4)_2$, a 2-oxopyrrolidin-1-yl group or a 2-oxoazepan-1-yl group, each $R^3$ is a hydrogen atom or a methyl group, and each $R^4$ represents a hydrogen atom, a $C_{1-4}$ alkyl group or a $(C_2H_4O)_qR^3$ group, with q being an integer varying between 1 and 10.

2. A polymer microparticle according to claim 1, wherein R is a group that is capable of releasing a $C_{6-15}$ perfuming aldehyde or ketone.

3. A polymer microparticle according to claim 1, wherein $R^1$ represents a $C_{2-9}$ hydrocarbon di-, tri- or tetra-radical optionally comprising 1, 2, 3 or 4 oxygen atoms.

4. A polymer microparticle according to claim 1, wherein $R^2$ represents a hydrogen atom and said $R^3$ represents a hydrogen atom.

5. A polymer microparticle according to claim 1, wherein $R^4$ represents a hydrogen atom, or one of a methyl, ethyl, propyl, isopropyl or butyl group.

6. A polymer microparticle according to claim 1, wherein x is 1.

7. A polymer microparticle according claim 1, wherein B represents a COOH, a $COOCH_3$, a $C_6H_5$, a $C_6H_4COOH$, a OH, a $CH_3COO$, a $CONH_2$, a 2-oxopyrrolidin-1-yl group or a 2-oxoazepan-1-yl group.

8. A polymer microparticle according to claim 1, having an average size of the particle comprised in the range between 100 nm and 100 μm.

9. A polymer microparticle according to claim 1, wherein one of the following units is present:
a repeating unit (I) obtained from the corresponding monomer (I') that has a Hansen solubility parameter comprised between 15 and 25 $(MPa)^{0.5}$;
a repeating unit (II) or (III) obtained from the corresponding monomer (II') or (III') that has a Hansen solubility parameter comprised between 10 and 29 $(MPa)^{0.5}$; or
a repeating unit (IV-a), (IV-b) or (IV-c) obtained from the corresponding monomer (IV-a'), (IV-b') or (IV-c') that has a Hansen solubility parameter comprised between 15 and 29 $(MPa)^{0.5}$
wherein (I'), (II'), (III'), (IV-a'), (IV-b') and (IV-c') have the following structures

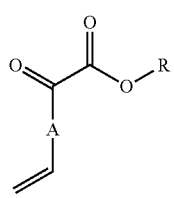

(I')

wherein A and R have the meaning indicated in formula (I);

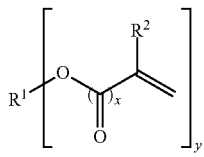
(II')

wherein x, y, R¹ and R² have the meaning indicated in formula (II);

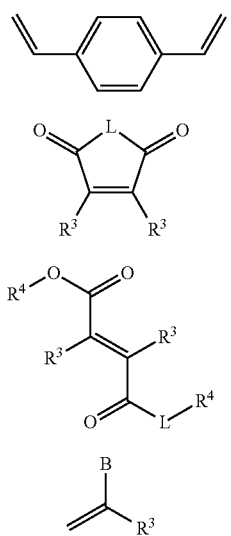

wherein L, R³, R⁴ and B have the meaning indicated in formulae (IV-a), (IV-b), (IV-c).

10. A perfuming composition comprising:
i) as perfuming ingredient, at least one polymer microparticle as defined in claim 1;
ii) at least one ingredient selected from the group consisting of a perfumery carrier and a perfumery base; and
iii) optionally at least one perfumery adjuvant.

11. A perfumed article comprising:
i) as perfuming ingredient, at least one polymer microparticle as defined in claim 1; and
ii) a consumer product base.

12. A perfumed article according to claim 11, wherein the consumer product base is one of a solid or liquid detergent, a fabric softener, a perfume, a cologne, an after-shave lotion, a perfumed soap, a shower salt, a bath salt, a mousse, an oil, a gel, a hygiene product, a hair care product, a shampoo, a body-care product, a deodorant, an antiperspirant, an air freshener, a cosmetic preparation, a fabric refresher, an ironing water, a paper, a wipe or a bleach.

13. The polymer microparticle of claim 1, wherein said perfuming aldehyde is selected from the group consisting of benzaldehyde, 1,3-benzodioxol-5-carboxaldehyde, 3-(1,3-benzodioxol-5-yl)-2-methylpropanal, 3-(4-tert-butyl-1-cyclohexen-1-yl)propanal, 2,4-decadienal, 2-decenal, 4-decenal, 8-decenal, 9-decenal, 3-(6,6-dimethyl-bicyclo[3.1.1]hept-2-en-2-yl)propanal, 2,4-dimethyl-3-cyclohexene-1-carbaldehyde, 3,5-dimethyl-3-cyclohexene-1-carbaldehyde, 1-(3,3-dimethyl-1-cyclohexyl)-1-ethanone, 5,9-dimethyl-4,8-decadienal, 3-(3,3-dimethyl-2,3-dihydro-1H-inden-5-yl)propanal, 3-(1,1-dimethyl-2,3-dihydro-1H-inden-5-yl)propanal, 2,6-dimethyl-5-heptenal, 3,7-dimethyl-2,6-octadienal, 3,7-dimethyloctanal, 3,7-dimethyl-6-octenal, (3,7-dimethyl-6-octenyl)acetaldehyde, 3-dodecenal, 4-dodecenal, 3-ethoxy-4-hydroxybenzaldehyde, 4-ethyl benzaldehyde, 3-(2-ethylphenyl)-2,2-dimethylpropanal, 3-(4-ethylphenyl)-2,2-dimethylpropanal, 2-furancarbaldehyde, 2,4-heptadienal, 3,5,5,6,7,8,8-heptamethyl-5,6,7,8-tetrahydronaphthalene-2-carbaldehyde, 4-heptenal, 2-hexenal, 3-hexenal, 2-hexyl-3-phenyl-2-propenal, 2-hydroxybenzaldehyde, 7-hydroxy-3,7-dimethyloctanal, 4-hydroxy-3-methoxybenzaldehyde, 4-(4-hydroxy-4-methylpentyl)-3-cyclohexene-1-carbaldehyde, 3-(4-hydroxy-4-methylpentyl)-3-cyclohexene-1-carbaldehyde, 4-isopropylbenzaldehyde, 8-isopropyl-6-methyl-bicyclo[2.2.2]oct-5-ene-2-carbaldehyde, 3-(4-isopropylphenyl)-2-methylpropanal, 2-(4-isopropylphenyl)propanal, 2-methoxybenzaldehyde, 4-methoxybenzaldehyde, 6-methoxy-2,6-dimethylheptanal, 3-(2-methoxyphenyl)acrylaldehyde, 8(9)-methoxy-tricyclo[5.2.1.0.(2,6)]decane-3(4)-carbaldehyde, 4-methylbenzaldehyde, 3-(4-methylcyclohex-3-en-1-yl)butanal, 2-(4-methylenecyclohexyl)propanal, 1-methyl-4-(4-methyl-3-pentenyl)-3-cyclohexen-1-carbaldehyde, 3-(4-methyl-3-pentenyl)-3-cyclohexene-1-carbaldehyde, 4-(4-methyl-3-pentenyl)-3-cyclohexene-1-carbaldehyde, (4-methylphenoxy) acetaldehyde, (4-methylphenyl) acetaldehyde, 3-methyl-5-phenylpentanal, 2-(1-methylpropyl)-1-cyclohexanone, 2-methyl-4-(2',2',3'-trimethyl-3'-cyclopentenyl)-4-pentenal, 2,4-nonadienal, 2,6-nonadienal, 2-nonenal, 3-nonenal, 6-nonenal, 8-nonenal, 2-octenal, 2-pentyl-3-phenyl-2-propenal, phenoxyacetaldehyde, 2-phenylacetaldehyde, 3-phenylbutanal, 3-phenylpropanal, 2-phenylpropanal, 3-phenyl-2-propenal, 4-(prop-1-en-2-yl)cyclohex-1-enecarbaldehyde, 3-(4-tert-butylphenyl)-2-methylpropanal, 3-(4-tert-butylphenyl)propanal, tricyclo[5.2.1.0(2,6)]decane-4-carbaldehyde, exo-tricyclo[5.2.1.0(2,6)]decane-8exo-carbaldehyde, 2,6,6-trimethyl -bicyclo[3.1.1]heptane-3-carbaldehyde, 2,4,6-trimethyl-3-cyclohexene-1-carbaldehyde, 3,5,6-trimethyl-3-cyclohexene-1-carbaldehyde, 2,2,3-trimethyl-3-cyclopentene-1-acetaldehyde, 2,6,10-trimethyl-2,6,9,11dodecatetraenal, 2,5,6-trimethyl-4-heptenal, 3,5,5-trimethylhexanal, 2,6,10-trimethyl-9-undecenal, 2-undecenal, 10-undecenal 9-undecenal, and an aldehyde of formula (R")CHO wherein R" is a linear or α-branched alkyl group of C6 to C15.

14. A perfuming composition comprising:
i) as perfuming ingredient, at least one polymer microparticle as defined in claim 13;
ii) at least one ingredient selected from the group consisting of a perfumery carrier and a perfumery base; and
iii) optionally at least one perfumery adjuvant.

15. A perfumed article comprising:
i) as perfuming ingredient, at least one polymer microparticle as defined in claim 13; and
ii) a consumer product base.

16. A perfumed article according to claim 15, wherein the consumer product base is one of a solid detergent, a liquid detergent, a fabric softener, a perfume, a cologne, an after-shave lotion, a perfumed soap, a shower salt, a bath salt, a mousse, an oil, a gel, a hygiene product, a hair care product, a shampoo, a body-care product, a deodorant, an antiperspirant, an air freshener, a cosmetic preparation, a fabric refresher, an ironing water, a paper, a wipe or a bleach.

17. The polymer microparticle of claim 1, wherein said perfuming ketone is selected from the group consisting of a damascenone, a damascone, an ionone, methyl ionone, irone, a macrocyclic ketone, cyclopentadecanone, 3-methyl-4-cyclopentadecen-1-one, 3-methyl-5-cyclopentadecen-1-one, 3-methyl-1-cyclopentadecanone, 1-(2-aminophenyl)-1-ethanone, 1-(3,3-dimethyl-1-cyclohexen-1-yl)-4-penten-1-one, 1-(5,5-dimethyl-1-cyclohexen-1-yl)-4-penten-1-one, 1-(3,3-dimethyl-1-cyclohexyl)-1-ethanone, 2,5-dimethyl-2-octene-6-one, 4,7-dimethyl-6-octene-3-one, (3,7-dimethyl-6-octenyloxy)acetaldehyde, 1-(2,4-dimethylphenyl)-1-ethanone, 4-(1,1-dimethylpropyl)-1-cyclohexanone, 2,4-di-tert-butyl-1-cyclohexanone, ethyl 4-oxopentanoate, 1-(4-ethylphenyl)-1-ethanone, 1-(3,5,5,6,8,8-hexamethyl-5,6,7,8-tetrahydronaphthalen-2-yl)ethanone, 2-hexyl-1-cyclopentanone, 2-hydroxy-3-methyl-2-cyclopenten-1-one, 4-(4-hydroxy-1-phenyl)-2-butanone (raspberry ketone), 1-(2-hydroxyphenyl)-1-ethanone, 1-(4-hydroxyphenyl)-1-ethanone, 2-isopropyl-5-methylcyclohexanone (menthone), 4-isopropyl-2-cyclohexen-1-one, 1-(5-isopropyl-2-methylcyclohex-1-en-1-yl)propanone, 1-(5-isopropyl-2-methylcyclohex-2-en-1-yl)propanone, 1-(4-isopropyl-1-phenyl)-1-ethanone, 2-(2-mercaptopropan-2-yl)-5-methylcyclohexanone, 1-(4-methoxyphenyl)-1-ethanone, 7-methyl-2H,4H-1,5-benzodioxepin-3-one, 5-methyl-3-heptanone, 6-methyl-5-hepten-2-one, methyl 3-oxo-2-pentyl-1-cyclopentaneacetate, 1-(4-methylphenyl)-1-ethanone (4-methylacetophenone), 5-methyl-2-(propan-2-ylidene)cyclohexanone, 5-methyl-2-(prop-1-en-2-yl)cyclohexanone, 2-methyl-5-(prop-1-en-2-yl)cyclohex-2-enone, 5-methyl-exo-tricyclo[6.2.1.0(2,7)]undecan-4-one, 3-methyl -4-(1,2,2-trimethylpropyl)-4-penten-2-one, 2-naphthalenyl-1-ethanone, 1-(octahydro-2,3,8,8-tetrame-2-naphthalenyl)-1-ethanone, 3,4,5,6,6-pentamethyl-3-hepten-2-one, 2-pentyl-1-cyclopentanone, 4-phenyl-2-butanone (benzylacetone), 1-phenyl-1-ethanone, 2-tert-butyl-1-cyclohexanone, 4-tert-butyl-1-cyclohexanone, 1-(4-tert-butylphenyl)-1-ethanone, 3,5,6,6-tetramethyl-4-methyleneheptan-2-one, 2,4,4,7-tetramethyl-6-octen-3-one, 1,7,7-trimethyl-bicyclo[2.2.1]heptan-2-one, 2,6,6-trimethyl-1-cycloheptanone, 2,6,6-trimethyl-2-cyclohexene-1,4-dione, 4-(2,6,6-trimethyl-2-cyclohexen-1-yl)-2-butanone, 1-(2,4,4-trimethyl-2-cyclohexen-1-yl)-2-buten-1-one, 1-(3,5,6-trimethyl-3-cyclohexen-1-yl)-1-ethanone, 2,2,5-trimethyl-5-pentyl-1-cyclopentanone and a C6-15 ketone of formula (R')(R")C=O wherein R' and R" are linear alkyl groups.

18. A perfuming composition comprising:
  i) as perfuming ingredient, at least one polymer microparticle as defined in claim 17;
  ii) at least one ingredient selected from the group consisting of a perfumery carrier and a perfumery base; and
  iii) optionally at least one perfumery adjuvant.

19. A perfumed article comprising:
  i) as perfuming ingredient, at least one polymer microparticle as defined in claim 17; and
  ii) a consumer product base.

20. A perfumed article according to claim 19, wherein the consumer product base is one of a solid detergent, a liquid detergent, a fabric softener, a perfume, a cologne, an aftershave lotion, a perfumed soap, a shower salt, a bath salt, a mousse, an oil, a gel, a hygiene product, a hair care product, a shampoo, a body-care product, a deodorant, an antiperspirant, an air freshener, a cosmetic preparation, a fabric refresher, an ironing water, a paper, a wipe or a bleach.

* * * * *